(12) United States Patent
Cardarelli et al.

(10) Patent No.: US 8,491,898 B2
(45) Date of Patent: *Jul. 23, 2013

(54) MONOCLONAL ANTIBODIES AGAINST CD30 LACKING IN FUCOSYL RESIDUES

(75) Inventors: Josephine M. Cardarelli, San Carlos, CA (US); Amelia Nancy Black, Los Gatos, CA (US)

(73) Assignee: Medarex, L.L.C., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,566

(22) Filed: May 2, 2012

(65) Prior Publication Data

US 2012/0251533 A1    Oct. 4, 2012

Related U.S. Application Data

(62) Division of application No. 11/918,178, filed as application No. PCT/US2006/005854 on Feb. 17, 2006, now Pat. No. 8,207,303.

(60) Provisional application No. 60/654,197, filed on Feb. 18, 2005.

(51) Int. Cl.
*A61K 39/395* (2006.01)
*A61K 39/44* (2006.01)

(52) U.S. Cl.
USPC .................. 424/133.1; 424/141.1; 424/143.1; 424/144.1; 424/178.1

(58) Field of Classification Search
None
See application file for complete search history.

(56) References Cited

U.S. PATENT DOCUMENTS

| | | | |
|---|---|---|---|
| 5,165,923 | A | 11/1992 | Thorpe et al. |
| 5,643,759 | A | 7/1997 | Pfreundschub et al. |
| 5,859,205 | A | 1/1999 | Adair et al. |
| 5,866,372 | A | 2/1999 | Stein et al. |
| 6,033,876 | A | 3/2000 | Lemke et al. |
| 6,143,869 | A | 11/2000 | Goodwin et al. |
| 6,632,927 | B2 | 10/2003 | Adair et al. |
| 7,387,776 | B2 | 6/2008 | Keler et al. |
| 2002/0064527 | A1 | 5/2002 | Mohler et al. |
| 2003/0157108 | A1 | 8/2003 | Presta |
| 2003/0175884 | A1* | 9/2003 | Umana et al. ............... 435/69.1 |
| 2004/0006215 | A1 | 1/2004 | Keler et al. |
| 2004/0110704 | A1 | 6/2004 | Yamane et al. |
| 2004/0156847 | A1* | 8/2004 | Miura et al. ............... 424/144.1 |
| 2004/0241817 | A1 | 12/2004 | Umana et al. |
| 2005/0054055 | A1 | 3/2005 | Kucherlapati et al. |
| 2006/0127392 | A1 | 6/2006 | de Romeuf et al. |
| 2006/0177442 | A1 | 8/2006 | Von Strandmann et al. |

FOREIGN PATENT DOCUMENTS

| | | |
|---|---|---|
| EP | 0613497 A1 | 9/1994 |
| EP | 0657533 A1 | 6/1995 |
| EP | 0805871 B1 | 11/1997 |
| EP | 1498485 A1 | 1/2005 |
| WO | 91/07437 A2 | 5/1991 |
| WO | 91/07941 A2 | 6/1991 |
| WO | 92/03918 A1 | 3/1992 |
| WO | 93/10232 A1 | 5/1993 |
| WO | 94/04189 A1 | 3/1994 |
| WO | 94/25585 A1 | 11/1994 |
| WO | 96/22384 A1 | 7/1996 |
| WO | 97/17374 A1 | 5/1997 |
| WO | 98/24884 A1 | 6/1998 |
| WO | 98/24893 A2 | 6/1998 |
| WO | 99/40187 A1 | 8/1999 |
| WO | 01/11059 A1 | 2/2001 |
| WO | 02/11767 A2 | 2/2002 |
| WO | 02/17979 A2 | 3/2002 |
| WO | 02/43661 A2 | 6/2002 |
| WO | 03/059282 A2 | 7/2003 |
| WO | 03/080672 A1 | 10/2003 |
| WO | 03/085107 A1 | 10/2003 |
| WO | 03/104432 A2 | 12/2003 |
| WO | 2004/029092 A2 | 4/2004 |
| WO | 2005/001038 A2 | 1/2005 |
| WO | 2005/014651 A1 | 2/2005 |
| WO | 2006/039644 A2 | 4/2006 |
| WO | 2006/089232 A2 | 8/2006 |

OTHER PUBLICATIONS

Giacomelli R, Passacantando A, Parzanese I, et al. Serum levels of soluble CD30 are increased in ulcerative colitis (UC) but not in Crohn's disease (CD). Clin Exp Immunol. 1998;111:532-535.*

Sun et al. CD30 Ligand Is a Target for a Novel Biological Therapy against Colitis Associated with Th17 Responses. The Journal of Immunology Dec. 15, 2010 vol. 185 No. 12 7671-7680.*

Sun X, Somada S, Shibata K, et al. A critical role of CD30 ligand/CD30 in controlling inflammatory bowel diseases in mice. Gastroenterology. 2008;134:447-458.*

Somada et al. CD30 Ligand/CD30 Interaction Is Involved in Pathogenesis of Inflammatory Bowel Disease. Dig Dis Sci (2012) 57:2031-2037.*

Biancone et al. Autoimmunity to tropomyosin isoforms in ulcerative colitis (UC) patients and unaffected relatives. Clin Exp Immunol 1998; 113:198-205.*

Ebert et al. Antibody to Tropomyosin Isoform 5 and Complement Induce the Lysis of Colonocytes in Ulcerative Colitis. Am J Gastroenterol. Dec. 2009;104(12):2996-3003.*

(Continued)

*Primary Examiner* — Maher Haddad
(74) *Attorney, Agent, or Firm* — Nelson Mullins Riley & Scarborough LLP; Jane E. Remillard, Esq.; Jill Gorny Sloper, Esq.

(57) ABSTRACT

The invention pertains to anti-CD30 antibodies that lack fucosyl residues. The antibodies of the invention exhibit increased antibody-dependent cellular cytotoxicity (ADCC) activity, including the ability to lyse CD30-expressing cell lines that are not lysed by the fucosylated form of the antibodies. The invention also provides host cells that express the anti-CD30 antibodies that lack fucosyl residues, wherein the host cells are deficient for a fucosyl transferase. Methods of using the antibodies to inhibit the growth of CD30+ cells, such as tumor cells, are also provided.

16 Claims, 15 Drawing Sheets

OTHER PUBLICATIONS

Sartor, RB. Mechanisms of disease: pathogenesis of Crohn's disease and ulcerative colitis. Nat Clin Pract Gastroenterol Hepatol. Jul. 2006;3(7):390-407.*

Chan et al. Therapeutic antibodies for autoimmunity and inflammation. Nat Rev Immunol. May 2010;10(5):301-16.*

Weng et al. Two immunoglobulin G fragment C receptor polymorphisms independently predict response to rituximab in patients with follicular lymphoma. J Clin Oncol. Nov. 1, 2003;21(21):3940-7.*

Pallesen, G., et al. "Ki-1 (CD30) antigen is regularly expressed by tumor cells of embryonal carcinoma" Am J Pathol. Dec. 1988;133(3):446-50.

Pallesen, G., et al. "The diagnostic significance of the CD30 (Ki-1) antigen" Histopathology Apr. 1990;16(4):409-13.

Panka, David J. et al., "Variable region framework differences result in decreased or increased affinity of variant anti-digoxin antibodies," Proc. Natl. Acad. Sci. USA, vol. 85:3080-3084 (1988).

Paul, William E., Fundamental Immunology, Third Edition, Raven Press, New York, pp. 292-295 (1993).

Pfreundschuh, M., et al. "Hodgkin and Reed-Sternberg cell associated monoclonal antibodies HRS-1 and HRS-2 react with activated cells of lymphoid and monocytoid origin" Anticancer Res. Mar.-Apr. 1988;8(2):217-24.

Piris, M., et al. "CD30 expression in non-Hodgkin's lymphoma" Histopathology Sep. 1990;17(3):211-8.

Pohl, C., et al. "CD30-specific AB1-AB2-AB3 internal image antibody network: potential use as anti-idiotype vaccine against Hodgkin's lymphoma" Int. J. Cancer May 28, 1993;54(3):418-25.

Press, O.W., et al. "Ricin A-chain containing immunotoxins directed against different epitopes on the CD2 molecule differ in their ability to kill normal and malignant T cells" J. Immunol. Dec. 15, 1988;141(12):4410-7.

Roeffen, Will F.G. et al., "Recombinant Human Antibodies Specific for the Pfs48/45 Protein of the Malaria Parasite *Plasmodium falciparum*," The Journal of Biological Chemistry, vol. 276(23):19807-19811 (2001).

Rudikoff, Stuart et al., "Single amino acid substitution altering antigen-binding specificity," Proc. Natl. Acad. Sci. USA, vol. 79:1979-1983 (1982).

Schnell, R., et al. "A Phase I study with an anti-CD30 ricin A-chain immunotoxin (Ki-4.dgA) in patients with refractory CD30+ Hodgkin's and non-Hodgkin's lymphoma" Clin. Cancer Res. Jun. 2002;8(6):1779-86.

Schwab, U., "Production of a monoclonal antibody specific for Hodgkin and Sternberg-Reed cells of Hodgkin's disease and a subset of normal lymphoid cells" Nature Sep. 2, 1982;299(5878):65-7.

Schwarting, R., et al. "BER-H2: a new anti-Ki-1 (CD30) monoclonal antibody directed at a formol-resistant epitope" Blood Oct. 1989;74(5):1678-89.

Shinkawa, Toyohide et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, vol. 278(5):3466-3473 (2003).

Stein, H., et al. "The expression of the Hodgkin's disease associated antigen Ki-1 in reactive and neoplastic lymphoid tissue: evidence that Reed-Sternberg cells and histiocytic malignancies are derived from activated lymphoid cells" Blood Oct. 1985;66(4):848-58.

Tian, Z. G., et al. "In vivo antitumor effects of unconjugated CD30 monoclonal antibodies on human anaplastic large-cell lymphoma xenografts" Cancer Res. Nov. 15, 1995;55(22):5335-41.

Tomlinson, Ian M. et al., "The Imprint of Somatic Hypermutation on the Repertoire of Human Germline V Genes," J. Mol. Biol., vol. 256:813-817 (1996).

Tsutsumi, Y., et al. "Site-specific chemical modification with polyethylene glycol of recombinant immunotoxin anti-Tac(Fv)-PE38 (LMB-2) improves antitumor activity and reduces animal toxicity and immunogenicity" PNAS 2000 97 (15):8548-8553.

Tutt, A. L., et al. "Monoclonal antibody therapy of B cell lymphoma: signaling activity on tumor cells appears more important than recruitment of effectors" J. Immunol. Sep. 15, 1998;161(6):3176-85.

Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).

Wahl, A., et al. "The anti-CD30 monoclonal antibody SGN-30 promotes growth arrest and DNA fragmentation in vitro and affects antitumor activity in models of Hodgkin's disease" Cancer Res. Jul. 1, 2002;62(13):3736-42.

Watanabe, Ken-ichiro et al, "Prevention of Etoposide-Induced Apoptosis by Proteaseome Inhibitors in a Human Leukemic Cell Line but Not in Fresh Acute Leukemia Blasts, A Differential Role of NF-kB Activation," Biochemical Pharmacology, vol. 60:823-830 (2000).

Wiens, Gregory D. et al., "Harmful somatic mutations: lessons from the dark side," Immunological Reviews, vol. 162:197-209 (1998).

Yamane-Ohnuki, Naoko et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering, vol. 87(5):614-622 (2004).

Yeung, S. Jim et al, "Ubiquitin-Proteasome Pathway Mediates Intracellular Degradation of Apolipoprotein B," Biochemistry, vol. 35:13843-13848 (1996).

Zheng, Bei et al, "Induction of Cell Cycle Arrest and Apoptosis by Proteasome Inhibitor PS-341 in Hodgkin Disease Cell Lines Is Independent of Inhibitor of Nuclear Factor-kB Mutations or Activation of the CD30, CD40, and RANK Receptors," Clinical Cancer Research, vol. 10:3207-3215 (2004).

Tamura, Midori et al., "Structural Correlates of an Anticarcinoma Antibody: Identification of a Specificity-Determining Residues (SDRs) and Development of a Minimally Immunogenic Antibody Variant by Retention of SDRs Only," The Journal of Immunology, vol. 164:1432-1441 (2000).

International Preliminary Report on Patentability for Application No. PCT/US2006/005854, dated Aug. 21, 2007.

International Search Report for Application No. PCT/US2005/035477, dated May 17, 2006.

International Search Report for Application No. PCT/US2006/005854, dated Nov. 11, 2006.

Almond, J.B. et al, "Proteasome inhibitor-induced apoptosis of B-chronic lymphocytic leukaemia cells involves cytochrome c release and caspase activation, accompanied by formation of an ~700 kDa Apaf-1 containing apoptosome complex," Leukemia, vol. 15:1388-1397 (2001).

An, J. et al, "Antitumor effects of bortezomib (PS-341) on primary effusion lymphomas," Leukemia, vol. 18:1699-1704 (2004).

Andreesen, R., et al. "A Hodgkin cell-specific antigen is expressed on a subset of auto- and alloactivated T (helper) lymphoblasts" Blood Jun. 1984; 63(6):1299-302.

Andreesen, R., et al. "Human macrophages can express the Hodgkin's cell-associated antigen Ki-1 (CD30)" Am. J. Pathol. Jan. 1989;134(1):187-92.

Barth, S., et al. "Ki-4(scFv)-ETA', a new recombinant anti-CD30 immunotoxin with highly specific cytotoxic activity against disseminated Hodgkin tumors in SCID mice" Blood Jun. 15, 2000;95(12):3909-14.

Beiboer, Sigrid H.W. et al., "Guided Selection of a Pan Carcinoma Specific Antibody Reveals Similar Binding Characteristics yet Structural Divergence Between the Original Murine Antibody and its Human Equivalent," J. Mol. Biol., vol. 296:833-849 (2000).

Berenbaum, M.C. et al., "Synergy, additivism and antagonism in immunosuppression, a critical review," Clin. Exp. Immunol., vol. 28:1-18 (1977).

Böll, Boris et al, "The fully human anti-CD30 antibody 5F11 activates Nf-kB and sensitizes lymphoma cells to bortezomib-induced apoptosis," Blood, vol. 106(5):1839-1842 (2005).

Borchmann, P., et al. "Phase 1 trial of the novel bispecific molecule H22xKi-4 in patients with refractory Hodgkin lymphoma" Blood Nov. 1, 2002;100(9):3101-7.

Borchmann, Peter et al, "The human anti-CD30 antibody 5F11 shows in vitro and in vivo activity against malignant lymphoma," Blood, vol. 102(10):3737-3742 (2003).

Bowen, M., et al. "Functional effects of CD30 on a large granular lymphoma cell line, YT. Inhibition of cytotoxicity, regulation of CD28 and IL-2R, and induction of homotypic aggregation" J Immunol. Dec. 1, 1993;151(11):5896-906.

Brown, McKay et al., "Tolerance to Single, but Not Multiple, Amino Acid Replacements in Antibody VH CDR2," The Journal of Immunology, vol. 156:3285-3291 (1996).

Burns, B., et al. "Ki-1-positive non-Hodgkin's lymphomas. An immunophenotypic, ultrastructural, and morphometric study" Am J Clin Pathol. Mar. 1990;93(3):327-32.

Byers, Tim, "What Can Randomized Controlled Trials Tell Us About Nutrition and Cancer Prevention?" CA Cancer J. Clin., vol. 49:353-361 (1999).

Carde, P., et al. "Immunoscintigraphy of Hodgkin's disease: In vivo use of radiolabelled monoclonal antibodies derived from Hodgkin cell lines" Eur J Cancer. Apr.1990;26(4):474-9.

Casset, Florence et al., "A peptide mimetic of an anti-CD4 monoclonal antibody by rational design," Biochemical and Biophysical Research Communications, vol. 307:198-205 (2003).

Chiarle, R., et al. "CD30 in normal and neoplastic cells" Clin Immunol. Feb. 1999;90(2):157-64.

Colman, P.M., "Effects of amino acid sequence changes on antibody-antigen interactions," Research in Immunology, vol. 145:33-36 (1994).

Clynes, Raphael A. et al., "Inhibitory Fc receptors modulate in vivo cytoxicity against tumor targets," Nature Medicine, vol. 6(4):443-446 (2000).

De Bruin, P.C. et al. "CD30 expression in normal and neoplastic lymphoid tissue: biological aspects and clinical implications" Leukemia Oct. 1995;9(10):1620-7.

Durkop, H., et al. "Molecular cloning and expression of a new member of the nerve growth factor receptor family that is characteristic for Hodgkin's disease" Cell Feb. 7, 1992;68(3):421-7.

Eckert, F., et al. "Follicular lymphoid hyperplasia of the skin with high content of Ki-1 positive lymphocytes" Am J Dermatopathol. Aug. 1989;11(4):345-52.

Engert, A., et al. "Antitumor effects of ricin A chain immunotoxins prepared from intact antibodies and Fab' fragments on solid human Hodgkin's disease tumors in mice" Cancer Res. May 15, 1990;50(10):2929-35.

Engert, A., et al. "Evaluation of ricin a chain-containing immunotoxins directed against the CD30 antigen as potential reagents for the treatment of Hodgkin's disease" Cancer Res. Jan. 1, 1990;50(1):84-8.

Engert, A., et al. "Treatment of advanced Hodgkin's lymphoma: standard and experimental approaches" Semin Hematol. Jul. 1999;36(3):282-9.

Falini, B., et al. "In vivo targeting of Hodgkin and Reed-Sternberg cells of Hodgkin's disease with monoclonal antibody Ber-H2 (CD30): immunohistological evidence" Br J Haematol. Sep. 1992;82(1):38-45.

Falini, B., et al. "Response of refractory Hodgkin's disease to monoclonal anti-CD30 immunotoxin" Lancet May 16, 1992;339(8803):1195-6.

Froese, P., et al. "Biochemical characterization and biosynthesis of the Ki-1 antigen in Hodgkin-derived and virus-transformed human B and T lymphoid cell lines" J Immunol. Sep. 15, 1987;139(6):2081-7.

Granziero, Luisa et al., "Adoptive immunotherapy prevents prostate cancer in a transgenic animal model," Eur. J. Immunol., vol. 29:1127-1138 (1999).

Gruss, H.J. et al. "Pleiotropic effects of the CD30 ligand on CD30-expressing cells and lymphoma cell lines" Blood Apr. 15, 1994;83(8):2045-56.

Hecht, T., et al. "Production and characterization of a monoclonal antibody that binds Reed-Sternberg cells" J Immunol. Jun. 1985;134(6):4231-6.

Heuck, Friederike et al, "Combination of the Human Anti-CD30 Antibody 5F11 with Cytostatic Drugs Enhances Its Antitumor Activity against Hodgkin and Anaplastic Large Cell Lymphoma Cell Lines," J. Immunother., vol. 27 (5):347-353 (2004).

Horie, Ryouichi et al, "Ligand-independent signaling by overexpressed CD30 drives NF-kB activation in Hodgkin-Reed-Sternberg cells," Oncogene, Vo. 21:2493-2503 (2002).

Horn-Lohrens, O., et al. "Shedding of the soluble form of CD30 from the Hodgkin-analogous cell line L540 is strongly inhibited by a new CD30-specific antibody (Ki-4)" Int J Cancer. Feb. 8, 1995;60(4):539-44.

Hsu, S.M., et al. "Effect of monoclonal antibodies anti-2H9, anti-IRac, and anti-HeFi-1 on the surface antigens of Reed-Sternberg cells" J Natl Cancer Inst. Nov. 1987;79(5):1091-9.

http://weisental.org/synergy1.htm, "Synergy analysis of 'classic' and newer drug combinations," (2008).

Hubinger, G., et al. "CD30-mediated cell cycle arrest associated with induced expression of p21(CIP1/WAF1) in the anaplastic large cell lymphoma cell line Karpas 299" Oncogene. Feb. 1, 2001;20(5):590-8.

Josimovic-Alasevic, O., et al. "Ki-1 (CD30) antigen is released by Ki-1-positive tumor cells in vitro and in vivo. I. Partial characterization of soluble Ki-1 antigen and detection of the antigen in cell culture supernatants and in serum by an enzyme-linked immunosorbent assay" Eur J Immunol. Jan. 1989;19(1):157-62.

Klimka, A. et al., "Human anti-CD30 recombinant antibodies by guided phage antibody selection using cell panning," British Journal of Cancer, vol. 83(2):252-260 (2000).

Koon, Henry B. et al., "Anti-CD30 antibody-based therapy," Current Opinion in Oncology, vol. 12:588-593 (2000).

Levi, Edi et al, "CD30-activation-mediated growth inhibition of anaplastic large-cell lymphoma cell lines: apoptosis or cell-cycle arrest?" Blood, vol. 98(5):1630-1632 (2001).

Lonberg, Nils et al., "Human Antibodies from Transgenic Mice," Intern. Rev. Immunol., vol. 13:65-93 (1995).

MacCallum, Robert M. et al., "Antibody-antigen Interactions: Contact Analysis and Binding Site Topography," J. Mol. Biol., vol. 262:732-745 (1996).

May, R. D., et al. "Evaluation of ricin A chain-containing immunotoxins directed against different epitopes on the delta-chain of cell surface-associated IgD on murine B cells" J Immunol. May 1, 1990;144(9):3637-42.

Mechtersheimer, G., et al. "Expression of Ki-1 antigen (CD30) in mesenchymal tumors,"Cancer Oct. 15, 1990;66 (8):1732-7.

Miettinen, M., "CD30 distribution. Immunohistochemical study on formaldehyde-fixed, paraffin-embedded Hodgkin's and non-Hodgkin's lymphomas" Arch Pathol Lab Med. Nov. 1992;116(11):1197-1201.

Mir, Samy S. et al, "Differential effects of CD30 activation in anaplastic large cell lymphoma and Hodgkin disease cells," Blood, vol. 96(13):4307-4312 (2000).

O'Connor, Owen A., "The Emerging Role of Bortezomib in the Treatment of Indolent Non-Hodgkin's and Mantle Cell Lymphomas," Current Treatment Options in Oncology, vol. 5:269-281 (2004).

Orlowski, Robert Z. et al., "Phase I Trial of the Proteasome Inhibitor PS-341 in Patients With Refractory Hematologic Malignancies," J. Clin. Oncol., vol. 20:4420-4427 (2002).

Padlan, Eduardo A., "Anatomy of the Antibody Molecule," Molecular Immunology, vol. 31(3):169-217 (1994).

\* cited by examiner

```
Anti-CD30 5F11 VH
    V-segment:     Locus: 4-34
    D segment:     Locus - 7-27
    J segment:     JH4b
```

|     | Q   | V   | Q   | L   | Q   | Q   | W   | G   | A   | G   | L   | L   | K   | P   | S   | E   | T   | L   |
| --- | --- | --- | --- | --- | --- | --- | --- | --- | --- | --- | --- | --- | --- | --- | --- | --- | --- | --- |
| 1   | CAG | GTG | CAG | CTA | CAG | CAG | TGG | GGC | GCA | GGA | CTG | TTG | AAG | CCT | TCG | GAG | ACC | CTG |

CDR1

|     | S   | L   | T   | C   | A   | V   | Y   | G   | G   | S   | F   | S   | A   | Y   | Y   | W   | S   | W   |
| --- | --- | --- | --- | --- | --- | --- | --- | --- | --- | --- | --- | --- | --- | --- | --- | --- | --- | --- |
| 55  | TCC | CTC | ACC | TGC | GCT | GTC | TAT | GGT | GGG | TCC | TTC | AGT | GCT | TAC | TAC | TGG | AGC | TGG |

CDR2

|     | I   | R   | Q   | P   | P   | G   | K   | G   | L   | E   | W   | I   | G   | D   | I   | N   | H   | G   |
| --- | --- | --- | --- | --- | --- | --- | --- | --- | --- | --- | --- | --- | --- | --- | --- | --- | --- | --- |
| 109 | ATC | CGC | CAG | CCC | CCA | GGG | AAG | GGG | CTG | GAG | TGG | ATT | GGG | GAC | ATC | AAT | CAT | GGT |

CDR2

|     | G   | G   | T   | N   | Y   | N   | P   | S   | L   | K   | S   | R   | V   | T   | I   | S   | V   | D   |
| --- | --- | --- | --- | --- | --- | --- | --- | --- | --- | --- | --- | --- | --- | --- | --- | --- | --- | --- |
| 163 | GGA | GGC | ACC | AAC | TAC | AAC | CCG | TCC | CTC | AAG | AGT | CGA | GTC | ACC | ATA | TCA | GTA | GAC |

|     | T   | S   | K   | N   | Q   | F   | S   | L   | K   | L   | N   | S   | V   | T   | A   | A   | D   | T   |
| --- | --- | --- | --- | --- | --- | --- | --- | --- | --- | --- | --- | --- | --- | --- | --- | --- | --- | --- |
| 217 | ACG | TCC | AAG | AAC | CAG | TTC | TCC | CTG | AAG | CTG | AAC | TCT | GTA | ACC | GCC | GCG | GAC | ACG |

CDR3

|     | A   | V   | Y   | Y   | C   | A   | S   | L   | T   | A   | Y   | W   | G   | Q   | G   | S   | L   | V   |
| --- | --- | --- | --- | --- | --- | --- | --- | --- | --- | --- | --- | --- | --- | --- | --- | --- | --- | --- |
| 271 | GCT | GTG | TAT | TAC | TGT | GCG | AGC | CTA | ACT | GCC | TAC | TGG | GGC | CAG | GGA | AGC | CTG | GTC |

D7-27/DHQ52   JH4b

|     | T   | V   | S   | S   |
| --- | --- | --- | --- | --- |
| 325 | ACC | GTC | TCC | TCA |

*Fig. 1A*

```
Anti-CD30 5F11 VL
    V-segment:      Locus: L15
    J segment:      JK5

D   I   Q   M   T   Q   S   P   T   S   L   S   A   S   V   G   D   R
  1     GAC ATC CAG ATG ACC CAG TCT CCA ACC TCA CTG TCT GCA TCT GTA GGA GAC AGA

CDR1
                                 ~~~~~~~~~~~~~~~~~~~~~~~~~~~~~~~~~~~~~~~~~~~~
        V   T   I   T   C   R   A   S   Q   G   I   S   S   W   L   T   W   Y
 55     GTC ACC ATC ACT TGT CGG GCG AGT CAG GGT ATT AGC AGC TGG TTA ACC TGG TAT

CDR2
                                                     ~~~~~~~~~~~~~~~~~~~~~~~~~
        Q   Q   K   P   E   K   A   P   K   S   L   I   Y   A   A   S   S   L
109     CAG CAG AAA CCA GAG AAA GCC CCT AAG TCC CTG ATC TAT GCT GCA TCC AGT TTG

CDR2
        ~~~~~~~~
        Q   S   G   V   P   S   R   F   S   G   S   G   S   G   T   D   F   T
163     CAA AGT GGG GTC CCA TCA AGG TTC AGC GGC AGT GGA TCT GGG ACA GAT TTC ACT

CDR3
                                                                     ~~~~~~~~~
        L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGC CAA CAG

CDR3
        ~~~~~~~~~~~~~~~~~~~~~~~~~~~~~~
        Y   D   S   Y   P   I   T   F   G   Q   G   T   R   L   E   I   K
271     TAT GAT AGT TAC CCT ATC ACC TTC GGC CAA GGG ACA CGA CTG GAG ATT AAA
                             ↳JK5
```

*Fig. 1B*

```
Anti-CD30 17G1 VH
    V-segment:      Locus: 3-07
    D segment:      Not Found
    J segment:      JH2

E   V   Q   L   V   E   S   G   G   G   L   V   Q   P   G   G   S   L
    1   GAG GTG CAG TTG GTG GAG TCT GGG GGA GGC TTG GTC CAG CCT GGG GGG TCC CTG

CDR1
                                                           ~~~~~~~~~~~~~~~~~~~
        R   L   S   C   V   A   S   G   F   T   F   S   N   S   W   M   S   W
    55  AGA CTC TCC TGT GTA GCC TCT GGA TTC ACC TTT AGT AAC TCT TGG ATG AGC TGG

CDR2
                                                           ~~~~~~~~~~~~~~~~~~~
        V   R   Q   A   P   G   K   G   L   E   W   V   A   N   I   N   E   D
    109 GTC CGC CAG GCT CCA GGG AAA GGG CTG GAG TGG GTG GCC AAC ATA AAC GAA GAT

CDR2
        ~~~~~~~~~~~~~~~~~~~~~~~~~~~~~~~~~~~~~~~~~~~~~~~~~~
        G   S   E   K   F   Y   V   D   S   V   K   G   R   F   T   F   S   R
    163 GGA AGT GAG AAA TTC TAT GTG GAC TCT GTG AAG GGC CGA TTC ACC TTC TCC AGA

D   N   A   E   N   S   L   Y   L   Q   M   N   S   L   R   A   E   D
    217 GAC AAC GCC GAG AAC TCA CTG TAT CTG CAA ATG AAC AGC CTG AGA GCC GAG GAC

CDR3
                                                   ~~~~~~~~~~~~~~~~~~~~~~~~~~~
        T   A   V   Y   Y   C   A   R   V   H   W   Y   F   H   L   W   G   R
    271 ACG GCT GTG TAT TAC TGT GCG AGG GTT CAT TGG TAC TTC CAT CTC TGG GGC CGT
                                            |
                                            └→ JH2

G   T   L   V   T   V   S   S
    325 GGC ACC CTG GTC ACT GTC TCC TCA
```

*Fig. 2A*

```
Anti-CD30 17G1 VL
    V-segment:       Locus: A27
    J segment:       JK1

E   I   V   L   T   Q   S   P   G   T   L   S   L   S   P   G   E   R
  1     GAA ATT GTG TTG ACG CAG TCT CCA GGC ACC CTG TCT TTG TCT CCA GGG GAA AGA

CDR1
                                ~~~~~~~~~~~~~~~~~~~~~~~~~~~~~~~~~~~~~~~~~~~~~~~
         A   T   L   S   C   R   A   S   Q   S   V   S   S   S   Y   L   A   W
 55     GCC ACC CTC TCC TGC AGG GCC AGT CAG AGT GTT AGC AGC AGC TAC TTA GCC TGG

CDR2
                                                                    ~~~~~~~~~~~~
         Y   Q   Q   K   P   G   Q   A·  P   R   L   L   I   Y   G   A   S   S
109     TAC CAG CAG AAA CCT GGC CAG GCT CCC AGG CTC CTC ATC TAT GGT GCA TCC AGC

CDR2
     ~~~~~~~~~~~~
         R   A   T   G   I   P   D   R   F   S   G   S   G   S   G   T   D   F
163     AGG GCC ACT GGC ATC CCA GAC AGG TTC AGT GGC AGT GGG TCT GGG ACA GAC TTC

CDR3
                                                                         ~~~~~
         T   L   T   I   S   S   L   E   P   E   D   F   A   V   Y   Y   C   Q
217     ACT CTC ACC ATC AGC AGC CTG GAG CCT GAA GAT TTT GCA GTG TAT TAC TGT CAG

CDR3
     ~~~~~~~~~~~~~~~~~~~~~~~~~~~~~~~
         Q   Y   G   S   S   P   W   T   F   G   Q   G   T   K   V   E   I   K
271     CAG TAT GGT AGC TCA CCG TGG ACG TTC GGC CAA GGG ACC AAG GTG GAA ATC AAA
                                 ↳ JK1
```

*Fig. 2B*

```
Anti-2H9 CD30 VH
    V-segment:      Locus: 4-34
    D segment:      Locus - 5-12
    J segment:      JH2

Q   V   Q   L   Q   Q   W   G   A   G   L   L   K   P   S   E   T   L
  1     CAG GTG CAG CTA CAG CAG TGG GGC GCA GGA CTG TTG AAG CCT TCG GAG ACC CTG

CDR1
                                                            ~~~~~~~~~~~~~~~~~~
        S   L   T   C   A   V   Y   G   G   S   F   S   G   Y   Y   W   S   W
 55     TCC CTC ACC TGC GCT GTC TAT GGT GGG TCC TTC AGT GGT TAC TAC TGG AGC TGG

CDR2
                                                        ~~~~~~~~~~~~~~~~~~~~
        I   R   Q   P   P   G   K   G   L   E   W   I   G   E   I   N   H   S
109     ATC CGC CAG CCC CCA GGG AAG GGG CTG GAG TGG ATT GGG GAA ATC AAT CAT AGT

CDR2
        ~~~~~~~~~~~~~~~~~~~~~~~~~~~~~~~~~~~~~~~~~~~~~~~~
        G   S   T   K   Y   T   P   S   L   K   S   R   V   T   I   S   V   D
163     GGA AGC ACC AAG TAC ACC CCG TCC CTC AAG AGC CGA GTC ACC ATA TCA GTA GAC

T   S   K   H   Q   F   S   L   K   L   S   S   V   T   A   A   D   T
217     ACG TCC AAG CAC CAA TTC TCC CTG AAG CTG AGC TCT GTG ACC GCC GCG GAC ACG

CDR3
                                        ~~~~~~~~~~~~~~~~~~~~~~~~~~~~~~~~~~~~~~
        A   V   Y   Y   C   A   R   E   T   V   Y   Y   F   D   L   W   G   R
271     GCT GTG TAT TAC TGT GCG AGA GAG ACT GTC TAC TAC TTC GAT CTC TGG GGC CGT
                                                    ↳ JH2

G   T   L   V   T   V   S   S
325     GGC ACC CTG GTC ACT GTC TCC TCA
```

*Fig. 3A*

```
Anti-2H9 CD30 VL
    V-segment:      Locus: L6
    J segment:      JK1

E   I   V   L   T   Q   S   P   A   T   L   S   L   S   P   G   E   R
  1     GAA ATT GTG TTG ACA CAG TCT CCA GCC ACC CTG TCT TTG TCT CCA GGG GAA AGA

CDR1
                                        ~~~~~~~~~~~~~~~~~~~~~~~~~~~~~~~~~~~~~~
        A   T   L   S   C   R   A   S   Q   S   V   S   S   N   L   A   W   Y
  55    GCC ACC CTC TCC TGC AGG GCC AGT CAG AGT GTA AGC AGC AAC TTA GCC TGG TAC

CDR2
                                                                    ~~~~~~~~~~~
        Q   Q   K   P   G   Q   A   P   R   L   L   I   Y   D   A   S   N   R
  109   CAA CAG AAA CCT GGC CAG GCT CCC AGG CTC CTC ATC TAT GAT GCA TCC AAC AGG

CDR2
        ~~~~~~~~~
        A   T   G   I   P   A   R   L   S   G   S   G   S   G   T   D   F   T
  163   GCC ACT GGC ATC CCA GCC AGG CTC AGT GGC AGT GGG TCT GGG ACA GAC TTC ACT

CDR3
                                                                        ~~~~~~~
        L   T   I   S   S   L   E   P   E   D   F   A   V   Y   Y   C   Q   Q
  217   CTC ACC ATC AGC AGC CTA GAG CCT GAA GAT TTT GCA GTT TAT TAC TGT CAA CAG

CDR3
        ~~~~~~~~~~~~~~~~~~~~~~~~~~~~~
        R   S   N   W   P   W   T   F   G   Q   G   T   K   V   E   I   K
  271   CGT AGC AAC TGG CCG TGG ACG TTC GGC CAA GGG ACC AAG GTG GAA ATC AAA
                            ↳ JK1
```

*Fig. 3B*

Heavy Chain Germline Sequences 4-34 Germline:     Q V Q L Q Q W G A G L L K P S E T L S L T C A V Y G G S F S G  G Y Y W S
                                                                                                      CDR1

CDR2
                 W I R Q P P G K G L E W I G E I N H S G S T N Y N P S L K S R V T I S

CDR3
                 V D T S K N Q F S L K L S S V T A A D T A V Y Y C A R

CDR1

3-07 Germline:     E V Q L V E S G G G L V Q P G G S L R L S C A A S G F T F S S Y W M S W CDR2
                 V R Q A P G K G L E W V A N I K Q D G S E K Y Y V D S V K G R F T I S R

Light Chain Germline Sequences

L6 germline:

```
                                                      CDR1
E I V L T Q S P A T L S L S P G E R A T L S C  RASQSVSSSYLA
                CDR2
WYQQKPGQAPRLLIY DASNRAT GIPARFSGSGSG
                          CDR3
TDFTLTISSLEPEDFAVYYC  QQRSNW
```

A27 Germline:

```
                                    CDR1                           CDR2
EIVLTQSPGTLSLSPGERATLSC  RASQSVSSSYLA  WYQQKPGQAPRLLIY  GASSRAT

CDR3
GIPDRFSGSGSGTDFTLTISRLEPEDFAVYYC  QQYGSS
```

L15 Germline:

```
                                   CDR1                         CDR2
DIQMTQSPSSLSASVGDRVTITC  RASQGISSWLA  WYQQKPEKAPKSLIY  AASSLQS

CDR3
GVPSRFSGSGSGTDFTLTISSLQPEDFATYYC  QQYNSY
```

*Fig. 8B*

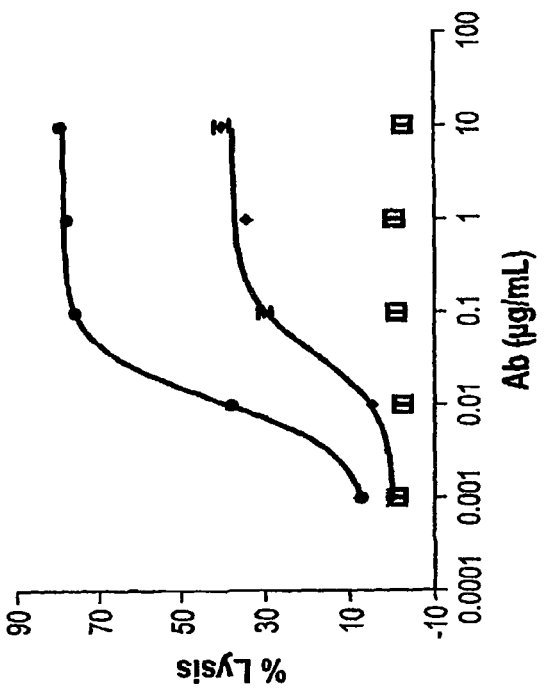
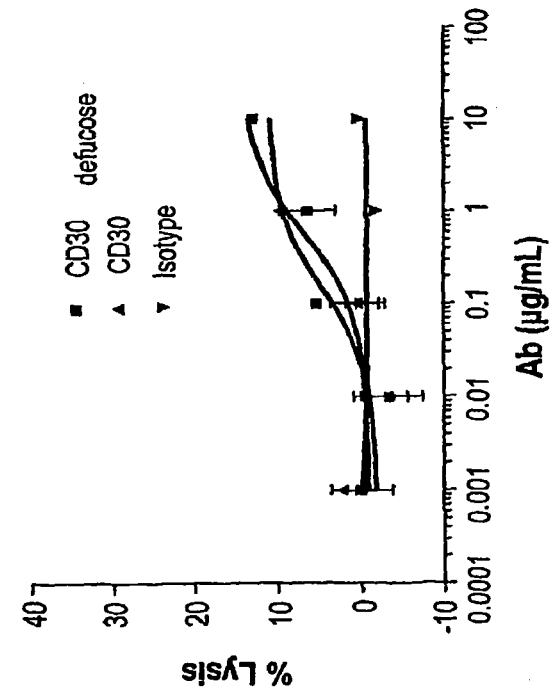
Fig. 10

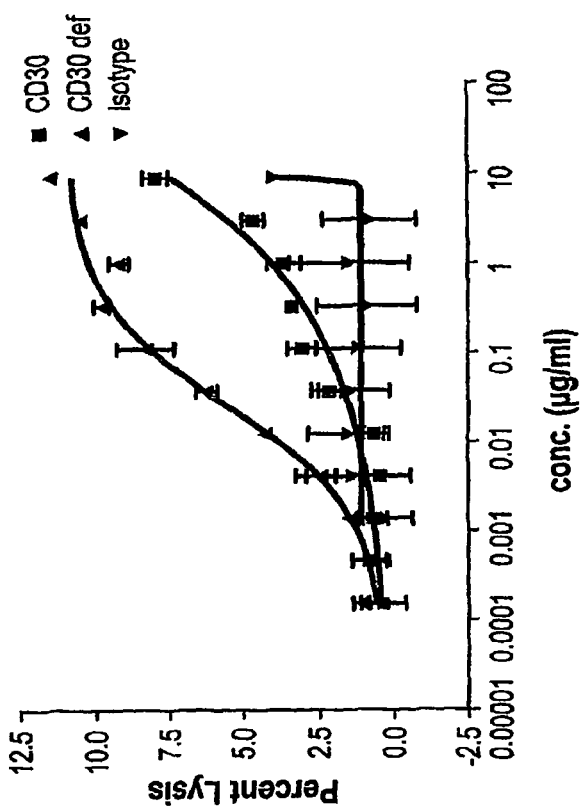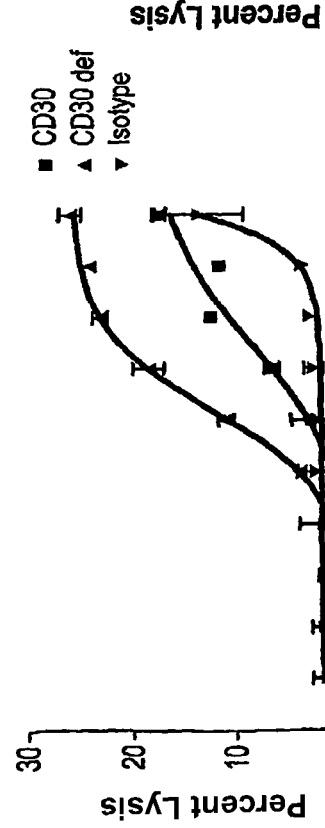
Fig. 11

US 8,491,898 B2

SEQUENCE LISTING

<160> NUMBER OF SEQ ID NOS: 35

<210> SEQ ID NO 1
<211> LENGTH: 112
<212> TYPE: PRT
<213> ORGANISM: Homo sapiens

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Asp Ile Asn His Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Ser Leu Thr Ala Tyr Trp Gly Gln Gly Ser Leu Val Thr Val Ser Ser
            100                 105                 110

<210> SEQ ID NO 2
<211> LENGTH: 116
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Ser
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Glu Lys Phe Tyr Val Asp Ser Val
    50                  55                  60

Lys Gly Arg Phe Thr Phe Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val His Trp Tyr Phe His Leu Trp Gly Arg Gly Thr Leu Val
            100                 105                 110

Thr Val Ser Ser
        115

<210> SEQ ID NO 3
<211> LENGTH: 116
<212> TYPE: PRT
<213> ORGANISM: Homo sapiens

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Lys Tyr Thr Pro Ser Leu Lys
    50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Val Tyr Tyr Phe Asp Leu Trp Gly Arg Gly Thr Leu Val
            100                 105                 110

Thr Val Ser Ser
        115

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Ile
                85                  90                  95

Thr Phe Gly Gln Gly Thr Arg Leu Glu Ile Lys
            100                 105

<210> SEQ ID NO 5
<211> LENGTH: 108
<212> TYPE: PRT
<213> ORGANISM: Homo sapiens

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile

-continued

```
                35                  40                  45
Tyr Asp Ala Ser Asn Arg Ala Thr Gly Ile Pro Ala Arg Leu Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys
            100                 105

<210> SEQ ID NO 7
<211> LENGTH: 5
<212> TYPE: PRT
<213> ORGANISM: Homo sapiens

<400> SEQUENCE: 7

Ala Tyr Tyr Trp Ser
 1               5

<210> SEQ ID NO 8
<211> LENGTH: 5
<212> TYPE: PRT
<213> ORGANISM: Homo sapiens

<400> SEQUENCE: 8

Asn Ser Trp Met Ser
 1               5

<210> SEQ ID NO 9
<211> LENGTH: 5
<212> TYPE: PRT
<213> ORGANISM: Homo sapiens

<400> SEQUENCE: 9

Gly Tyr Tyr Trp Ser
 1               5

<210> SEQ ID NO 10
<211> LENGTH: 16
<212> TYPE: PRT
<213> ORGANISM: Homo sapiens

<400> SEQUENCE: 10

Asp Ile Asn His Gly Gly Gly Thr Asn Tyr Asn Pro Ser Leu Lys Ser
 1               5                  10                  15

<210> SEQ ID NO 11
<211> LENGTH: 17
<212> TYPE: PRT
<213> ORGANISM: Homo sapiens

<400> SEQUENCE: 11

Asn Ile Asn Glu Asp Gly Ser Glu Lys Phe Tyr Val Asp Ser Val Lys
 1               5                  10                  15

Gly

<210> SEQ ID NO 12
<211> LENGTH: 16
<212> TYPE: PRT
<213> ORGANISM: Homo sapiens

<400> SEQUENCE: 12

Glu Ile Asn His Ser Gly Ser Thr Lys Tyr Thr Pro Ser Leu Lys Ser
```

1               5                  10                  15

<210> SEQ ID NO 13
<211> LENGTH: 4
<212> TYPE: PRT
<213> ORGANISM: Homo sapiens

<400> SEQUENCE: 13

Leu Thr Ala Tyr
 1

<210> SEQ ID NO 14
<211> LENGTH: 7
<212> TYPE: PRT
<213> ORGANISM: Homo sapiens

<400> SEQUENCE: 14

Val His Trp Tyr Phe His Leu
 1               5

<210> SEQ ID NO 15
<211> LENGTH: 8
<212> TYPE: PRT
<213> ORGANISM: Homo sapiens

<400> SEQUENCE: 15

Glu Thr Val Tyr Tyr Phe Asp Leu
 1               5

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Ser Trp Leu Thr
 1               5                  10

<210> SEQ ID NO 17
<211> LENGTH: 12
<212> TYPE: PRT
<213> ORGANISM: Homo sapiens

<400> SEQUENCE: 17

Arg Ala Ser Gln Ser Val Ser Ser Ser Tyr Leu Ala
 1               5                  10

<210> SEQ ID NO 18
<211> LENGTH: 11
<212> TYPE: PRT
<213> ORGANISM: Homo sapiens

<400> SEQUENCE: 18

Arg Ala Ser Gln Ser Val Ser Ser Asn Leu Ala
 1               5                  10

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
 1               5

```
<210> SEQ ID NO 20
<211> LENGTH: 7
<212> TYPE: PRT
<213> ORGANISM: Homo sapiens

<400> SEQUENCE: 20

Gly Ala Ser Ser Arg Ala Thr
1               5

<210> SEQ ID NO 21
<211> LENGTH: 7
<212> TYPE: PRT
<213> ORGANISM: Homo sapiens

<400> SEQUENCE: 21

Asp Ala Ser Asn Arg Ala Thr
1               5

<210> SEQ ID NO 22
<211> LENGTH: 9
<212> TYPE: PRT
<213> ORGANISM: Homo sapiens

<400> SEQUENCE: 22

Gln Gln Tyr Asp Ser Tyr Pro Ile Thr
1               5

<210> SEQ ID NO 23
<211> LENGTH: 9
<212> TYPE: PRT
<213> ORGANISM: Homo sapiens

<400> SEQUENCE: 23

Gln Gln Tyr Gly Ser Ser Pro Trp Thr
1               5

<210> SEQ ID NO 24
<211> LENGTH: 9
<212> TYPE: PRT
<213> ORGANISM: Homo sapiens

<400> SEQUENCE: 24

Gln Gln Arg Ser Asn Trp Pro Trp Thr
1               5

<210> SEQ ID NO 25
<211> LENGTH: 97
<212> TYPE: PRT
<213> ORGANISM: Homo sapiens

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg

<210> SEQ ID NO 26
<211> LENGTH: 98
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 27
<211> LENGTH: 94
<212> TYPE: PRT
<213> ORGANISM: Homo sapiens

<400> SEQUENCE: 27

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp
                85                  90

<210> SEQ ID NO 28
<211> LENGTH: 95
<212> TYPE: PRT
<213> ORGANISM: Homo sapiens

<400> SEQUENCE: 28

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser

<210> SEQ ID NO 29
<211> LENGTH: 94
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr
                 85                  90

<210> SEQ ID NO 30
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 30 cag gtg cag cta cag cag tgg ggc gca gga ctg ttg aag cct tcg gag     48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt gct tac     96
Thr Leu Ser Leu Thr Cys Ala Val Tyr Gly Gly Ser Phe Ser Ala Tyr
             20                  25                  30 tac tgg agc tgg atc cgc cag ccc cca ggg aag ggg ctg gag tgg att    144
Tyr Trp Ser Trp Ile Arg Gln Pro Pro Gly Lys Gly Leu Glu Trp Ile
         35                  40                  45 ggg gac atc aat cat ggt gga ggc acc aac tac aac ccg tcc ctc aag    192
Gly Asp Ile Asn His Gly Gly Gly Thr Asn Tyr Asn Pro Ser Leu Lys
     50                  55                  60 agt cga gtc acc ata tca gta gac acg tcc aag aac cag ttc tcc ctg    240
Ser Arg Val Thr Ile Ser Val Asp Thr Ser Lys Asn Gln Phe Ser Leu
 65                  70                  75                  80 aag ctg aac tct gta acc gcc gcg gac acg gct gtg tat tac tgt gcg    288
Lys Leu Asn Ser Val Thr Ala Ala Asp Thr Ala Val Tyr Tyr Cys Ala
                 85                  90                  95 agc cta act gcc tac tgg ggc cag gga agc ctg gtc acc gtc tcc tca    336
Ser Leu Thr Ala Tyr Trp Gly Gln Gly Ser Leu Val Thr Val Ser Ser
            100                 105                 110

<210> SEQ ID NO 31
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 31 gag gtg cag ttg gtg gag tct ggg gga ggc ttg gtc cag cct ggg ggg     48
Glu Val Gln Leu Val Glu Ser Gly Gly Gly Leu Val Gln Pro Gly Gly

```
tcc ctg aga ctc tcc tgt gta gcc tct gga ttc acc ttt agt aac tct     96
Ser Leu Arg Leu Ser Cys Val Ala Ser Gly Phe Thr Phe Ser Asn Ser
            20                  25                  30 tgg atg agc tgg gtc cgc cag gct cca ggg aaa ggg ctg gag tgg gtg    144
Trp Met Ser Trp Val Arg Gln Ala Pro Gly Lys Gly Leu Glu Trp Val
        35                  40                  45 gcc aac ata aac gaa gat gga agt gag aaa ttc tat gtg gac tct gtg    192
Ala Asn Ile Asn Glu Asp Gly Ser Glu Lys Phe Tyr Val Asp Ser Val
    50                  55                  60 aag ggc cga ttc acc ttc tcc aga gac aac gcc gag aac tca ctg tat    240
Lys Gly Arg Phe Thr Phe Ser Arg Asp Asn Ala Glu Asn Ser Leu Tyr
 65             70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
            85                  90                  95 gcg agg gtt cat tgg tac ttc cat ctc tgg ggc cgt ggc acc ctg gtc    336
Ala Arg Val His Trp Tyr Phe His Leu Trp Gly Arg Gly Thr Leu Val
        100                 105                 110 act gtc tcc tca                                                    348
Thr Val Ser Ser
    115

<210> SEQ ID NO 32
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 32 cag gtg cag cta cag cag tgg ggc gca gga ctg ttg aag cct tcg gag     48
Gln Val Gln Leu Gln Gln Trp Gly Ala Gly Leu Leu Lys Pro Ser Glu
  1               5                  10                  15 acc ctg tcc ctc acc tgc gct gtc tat ggt ggg tcc ttc agt ggt tac     96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att    144
Tyr Trp Ser Trp Ile Arg Gln Pro Pro Gly Lys Gly Leu Glu Trp Ile
        35                  40                  45 ggg gaa atc aat cat agt gga agc acc aag tac acc ccg tcc ctc aag    192
Gly Glu Ile Asn His Ser Gly Ser Thr Lys Tyr Thr Pro Ser Leu Lys
    50                  55                  60 agc cga gtc acc ata tca gta gac acg tcc aag cac caa ttc tcc ctg    240
Ser Arg Val Thr Ile Ser Val Asp Thr Ser Lys His Gln Phe Ser Leu
 65                 70                  75                  80 aag ctg agc tct gtg acc gcc gcg gac acg gct gtg tat tac tgt gcg    288
Lys Leu Ser Ser Val Thr Ala Ala Asp Thr Ala Val Tyr Tyr Cys Ala
            85                  90                  95 aga gag act gtc tac tac ttc gat ctc tgg ggc cgt ggc acc ctg gtc    336
Arg Glu Thr Val Tyr Tyr Phe Asp Leu Trp Gly Arg Gly Thr Leu Val
        100                 105                 110 act gtc tcc tca                                                    348
Thr Val Ser Ser
    115

<210> SEQ ID NO 33
<211> LENGTH: 321
<212> TYPE: DNA
<213> ORGANISM: Homo sapiens
<220> FEATURE:
<221> NAME/KEY: CDS
```

<222> LOCATION: (1)..(321)

<400> SEQUENCE: 33

```
gac atc cag atg acc cag tct cca acc tca ctg tct gca tct gta gga     48
Asp Ile Gln Met Thr Gln Ser Pro Thr Ser Leu Ser Ala Ser Val Gly
 1               5                  10                  15 gac aga gtc acc atc act tgt cgg gcg agt cag ggt att agc agc tgg     96
Asp Arg Val Thr Ile Thr Cys Arg Ala Ser Gln Gly Ile Ser Ser Trp
             20                  25                  30 tta acc tgg tat cag cag aaa cca gag aaa gcc cct aag tcc ctg atc    144
Leu Thr Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat gat agt tac cct atc    288
Glu Asp Phe Ala Thr Tyr Tyr Cys Gln Gln Tyr Asp Ser Tyr Pro Ile
                 85                  90                  95 acc ttc ggc caa ggg aca cga ctg gag att aaa                        321
Thr Phe Gly Gln Gly Thr Arg Leu Glu Ile Lys
            100                 105
```

<210> SEQ ID NO 34
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 34

```
gaa att gtg ttg acg cag tct cca ggc acc ctg tct ttg tct cca ggg     48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc     96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc agc ctg gag    240
Gly Ser Gly Ser Gly Thr Asp Phe Thr Leu Thr Ile Ser Ser Leu Glu
 65                  70                  75                  80 cct gaa gat ttt gca gtg tat tac tgt cag cag tat ggt agc tca ccg    288
Pro Glu Asp Phe Ala Val Tyr Tyr Cys Gln Gln Tyr Gly Ser Ser Pro
                 85                  90                  95 tgg acg ttc ggc caa ggg acc aag gtg gaa atc aaa                    324
Trp Thr Phe Gly Gln Gly Thr Lys Val Glu Ile Lys
            100                 105
```

<210> SEQ ID NO 35
<211> LENGTH: 321
<212> TYPE: DNA
<213> ORGANISM: Homo sapiens
<220> FEATURE:
<221> NAME/KEY: CDS
<222> LOCATION: (1)..(321)

```
<400> SEQUENCE: 35 gaa att gtg ttg aca cag tct cca gcc acc ctg tct ttg tct cca ggg        48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gta agc agc aac        96
Glu Arg Ala Thr Leu Ser Cys Arg Ala Ser Gln Ser Val Ser Ser Asn
                 20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
             35                  40                  45 tat gat gca tcc aac agg gcc act ggc atc cca gcc agg ctc agt ggc       192
Tyr Asp Ala Ser Asn Arg Ala Thr Gly Ile Pro Ala Arg Leu Ser Gly
         50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca gtt tat tac tgt caa cag cgt agc aac tgg ccg tgg       288
Glu Asp Phe Ala Val Tyr Tyr Cys Gln Gln Arg Ser Asn Trp Pro Trp
                     85                  90                  95 acg ttc ggc caa ggg acc aag gtg gaa atc aaa                           321
Thr Phe Gly Gln Gly Thr Lys Val Glu Ile Lys
                100                 105
```

MONOCLONAL ANTIBODIES AGAINST CD30 LACKING IN FUCOSYL RESIDUES

RELATED APPLICATIONS

This application is a divisional of U.S. patent application Ser. No. 11/918,178, filed Mar. 12, 2009, now U.S. Pat. No. 8,207,303, which is a U.S. 371 national phase of International Patent Application No.: PCT/US2006/005854, filed on Feb. 17, 2006, which claims the benefit of U.S. Provisional Application No. 60/654,197, filed on Feb. 18, 2005, the entire contents of which are incorporated herein in their entirety by this reference.

BACKGROUND OF THE INVENTION

The CD30 cell surface molecule is a member of the tumor necrosis factor receptor (TNF-R) superfamily. This family of molecules has variable homology among its members and includes nerve growth factor receptor (NGFR), CD120(a), CD120(b), CD27, CD40 and CD95. These molecules are typically characterized by the presence of multiple cysteine-rich repeats in the extracytoplasmic region (de Bruin, P. C., et al. *Leukemia* 9:1620-1627 (1995)). Members of this family are considered crucial for regulating proliferation and differentiation of lymphocytes.

CD30 is a type I transmembrane glycoprotein with six (human) or three (murine and rat) cysteine-rich repeats with a central hinge sequence. CD30 exists as a 120 kDa membrane molecule which develops from an intercellular precursor protein of 90 kDa. It is shed from the cell surface as a soluble protein (sCD30) of approximately 90 kDa. Shedding of sCD30 occurs as an active process of viable CD30 cells and is not merely caused by the release from dying or dead cells. cDNAs encoding the CD30 protein have been cloned from expression libraries of the HLTV-1 human T-cell line HUT-102 by immunoscreening with monoclonal antibodies Ki-1 and Ber-H2 (Schwab, U., et al. *Nature* 299:65 (1982)). The mouse and rat CD30 cDNA has been found to encode 498 and 493 amino acids, respectively. Human CD30 cDNA encodes an additional 90 amino acids, partially duplicated from one of the cysteine rich domains. The CD30 gene has been mapped to 1p36 in humans and 5q36.2 in rats.

CD30 is preferentially expressed by activated lymphoid cells. Specifically, stimulation of CD30 in lymphoid cells has been shown to induce pleiotropic biological effects, including proliferation, activation, differentiation and cell death, depending on cell type, stage of differentiation and presence of other stimuli (Gruss, H. J. et al., *Blood* 83:2045-2056 (1994)). CD30 was originally identified by the monoclonal antibody Ki-1, which is reactive with antigens expressed on Hodgkin and Reed-Sternberg cells of Hodgkin's disease (Schwab et al., *Nature* 299:65 (1982)). Accordingly, CD30 is widely used as a clinical marker for Hodgkin's lymphoma and related hematological malignancies (Froese et al., *J. Immunol.* 139:2081 (1987); Carde et al., *Eur. J. Cancer* 26:474 (1990)).

CD30 was subsequently shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas (Stein et al., *Blood* 66:848 (1985); Miettinen, *Arch. Pathol. Lab. Med.* 116:1197 (1992); Piris et al., *Histopathology* 17:211 (1990); Burns et al., *Am. J. Clin. Pathol.* 93:327 (1990); and Eckert et al., *Am. J. Dermatopathol.* 11:345 (1989)), as well as several virally-transformed lines such as human T-Cell Lymphotrophic Virus I or II transformed T-cells, and Epstein-Barr Virus transformed B-cells (Stein et al., *Blood* 66:848 (1985); Andreesen et al., *Blood* 63:1299 (1984)). In addition, CD30 expression has been documented in embryonal carcinomas, nonembryonal carcinomas, malignant melanomas, mesenchymal tumors, and myeloid cell lines and macrophages at late stages of differentiation (Schwarting et al., *Blood* 74:1678 (1989); Pallesen et al., *Am J. Pathol.* 133:446 (1988); Mechtersheimer et al., *Cancer* 66:1732 (1990); Andreesen et al., *Am. J. Pathol.* 134:187 (1989)).

Since the percentage of CD30-positive cells in normal individuals is quite small, the expression of CD30 in tumor cells renders it an important target for antibody mediated therapy to specifically target therapeutic agents against CD30-positive neoplastic cells (Chaiarle, R., et al. *Clin. Immunol.* 90(2):157-164 (1999)). Antibody mediated therapy has been shown to increase cytotoxicity of CD30-positive cells by both complement activation and antibody dependent cellular cytotoxicity (ADCC) (Pohl C., et al. *Int J Cancer* 54:418 (1993)). However, while the results obtained to date clearly establish CD30 as a useful target for immunotherapy, they also show that currently available murine antibodies do not constitute ideal therapeutic agents. Passive antibody therapy has not been effective in vitro or in vivo against patients with refractory Hodgkin's disease. A clinical trial of the anti-CD30 antibody Ber-H2 showed localization of the antibody, but no responses (Falini B. et al. (1992) *Brit J Haematol.* 82:38-45; Koon, H. B. et al. (2000) *Curr Opin in Oncol.* 12:588-593). Through coupling of an anti-CD30 antibody to a deglycosylated Ricin toxin-A chain toxin, cytotoxicity was shown in the treatment of human Hodgkin's Disease in a SCID mouse model, although grade 3 toxicities were also seen in the subjects (Schell, R. et al. (2002) *Annals of Oncology* 13:57-66).

Accordingly, the need exists for improved therapeutic antibodies against CD30 which are more effective for treating and/or preventing diseases mediated by CD30.

SUMMARY OF THE INVENTION

The present invention provides isolated defucosylated antibodies (i.e., antibodies lacking fucose residues) that bind to human CD30 and exhibit enhanced antibody directed cellular cytotoxic (ADCC) killing of CD30-expressing cells, as compared to the non-defucosylated form of the antibody (i.e., antibodies containing fucose residues). Also provided are methods for treating a variety of diseases involving CD30 expression using the antibodies and compositions of the invention.

In one aspect, the invention pertains to an isolated defucosylated monoclonal antibody, or an antigen-binding portion thereof, wherein the antibody binds to human CD30 with a $K_D$ of $10 \times 10^{-8}$ M or less, more preferably $1 \times 10^{-8}$ M or less, more preferably $5 \times 10^{-9}$ or less or even more preferably, $1 \times 10^{-9}$ or less.

The defucosylated antibodies of the present invention bind to CD30 and inhibit the growth of cells expressing CD30 by enhancing antibody dependent cellular cytotoxicity (ADCC) in the presence of human effector cells (e.g., monocytes or mononuclear cells), as compared to the fucosylated form of the antibody. In one embodiment, the defucosylated antibody mediates increased ADCC of cells expressing CD30 in the presence of human effector cells but not in the presence of mouse effector cells.

In a preferred embodiment, a defucosylated antibody of the invention induces ADCC of L1236 cells in vitro wherein the fucosylated form of the antibody does not induce ADCC, under conditions of an antibody concentration of 0.1 µg/ml and a target cell to effector cell ratio of 1:50. In another preferred embodiment, a defucosylated antibody of the invention enhances ADCC of L540, L428 and Karpas cells in vitro compared to the fucosylated form of the antibody, under conditions of an antibody concentration of 0.1 µg/ml and a target cell to effector cell ratio of 1:50. Accordingly, the antibodies of the present invention provide an improved means for treating disorders characterized by CD30 expression.

Preferably, the defucosylated antibody of the invention is a monoclonal antibody. In one aspect, the invention pertains to a humanized or chimeric monoclonal antibody. Preferably, the humanized or chimeric antibody is prepared from a mouse anti-CD30 antibody selected from the group consisting of: AC10, HeFi-1, Ber-H2, Ki-1, Ki-4, HRS-3, Irac, HRS-4, M44, M67, Ber-H8. In another aspect, the invention pertains to a human monoclonal antibody.

In one embodiment of the invention, the human monoclonal antibody comprises:
  (a) a heavy chain variable region comprising an amino acid sequence selected from the group consisting of SEQ ID NOs: 1, 2 and 3; and
  (b) a light chain variable region comprising an amino acid sequence selected from the group consisting of SEQ ID NOs: 4, 5 and 6.
  wherein the antibody binds CD30 and lacks fucose residues.

A preferred combination comprises:
  (a) a heavy chain variable region comprising the amino acid sequence of SEQ ID NO: 1; and
  (b) a light chain variable region comprising the amino acid sequence of SEQ ID NO: 4.

Another preferred combination comprises:
  (a) a heavy chain variable region comprising the amino acid sequence of SEQ ID NO: 2; and
  (b) a light chain variable region comprising the amino acid sequence of SEQ ID NO: 5.

Another preferred combination comprises:
  (a) a heavy chain variable region comprising the amino acid sequence of SEQ ID NO: 3; and
  (b) a light chain variable region comprising the amino acid sequence of SEQ ID NO: 6.

In another aspect, the invention provides a defucosylated anti-CD30 antibody comprising:
  a heavy chain variable region that comprises CDR1, CDR2, and CDR3 sequences; and a light chain variable region that comprises CDR1, CDR2, and CDR3 sequences, wherein:
  (a) the heavy chain variable region CDR1 sequence comprises an amino acid sequence selected from the group consisting of amino acid sequences of SEQ ID NOs: 7, 8, and 9;
  (b) the heavy chain variable region CDR2 sequence comprises an amino acid sequence selected from the group consisting of amino acid sequences of SEQ ID NOs: 10, 11, and 12;
  (c) the heavy chain variable region CDR3 sequence comprises an amino acid sequence selected from the group consisting of amino acid sequences of SEQ ID NOs: 13, 14, and 15;
  (a) the light chain variable region CDR1 sequence comprises an amino acid sequence selected from the group consisting of amino acid sequences of SEQ ID NOs: 16, 17, and 18;
  (a) the light chain variable region CDR2 sequence comprises an amino acid sequence selected from the group consisting of amino acid sequences of SEQ ID NOs: 19, 20, and 21; and
  (a) the light chain variable region CDR3 sequence comprises an amino acid sequence selected from the group consisting of amino acid sequences of SEQ ID NOs: 22, 23, and 24;
  wherein the antibody binds CD30 and lacks fucose residues.

A preferred combination comprises:
  (a) a human heavy chain variable region CDR1 comprising SEQ ID NO:7;
  (b) a human heavy chain variable region CDR2 comprising SEQ ID NO:10;
  (c) a human heavy chain variable region CDR3 comprising SEQ ID NO:13;
  (d) a human light chain variable region CDR1 comprising SEQ ID NO:16;
  (e) a human light chain variable region CDR2 comprising SEQ ID NO:19; and
  (f) a human light chain variable region CDR3 comprising SEQ ID NO:22.

Another preferred combination comprises:
  (a) a human heavy chain variable region CDR1 comprising SEQ ID NO:8;
  (b) a human heavy chain variable region CDR2 comprising SEQ ID NO:11;
  (c) a human heavy chain variable region CDR3 comprising SEQ ID NO:14;
  (d) a human light chain variable region CDR1 comprising SEQ ID NO:17;
  (e) a human light chain variable region CDR2 comprising SEQ ID NO:20; and
  (f) a human light chain variable region CDR3 comprising SEQ ID NO:23.

Yet another preferred combination comprises:
  (a) a human heavy chain variable region CDR1 comprising SEQ ID NO:9;
  (b) a human heavy chain variable region CDR2 comprising SEQ ID NO:12;
  (c) a human heavy chain variable region CDR3 comprising SEQ ID NO:15;
  (d) a human light chain variable region CDR1 comprising SEQ ID NO:18;
  (e) a human light chain variable region CDR2 comprising SEQ ID NO:21; and
  (f) a human light chain variable region CDR3 comprising SEQ ID NO:24.

In another aspect, the invention provides a defucosylated human anti-CD30 antibody which comprises a heavy chain variable region that is a product of or derived from a human $V_H$ 4-34 or $V_H$ 3-07 gene. The invention also provides a defucosylated human anti-CD30 antibody which comprises a light chain variable region that is a product of or derived from a human $V_k$ L15, A27 or L6 gene. The invention still further provides a defucosylated human anti-CD30 antibody which comprises a heavy chain variable region that is a product of or derived from a human $V_H$ 4-34 or $V_H$ 3-07 gene and a light chain variable region that is a product of or derived from a human $V_k$ L15, A27 or L6 gene.

In another aspect, the invention pertains to a host cell comprising immunoglobulin heavy and light chain genes encoding an anti-CD30 antibody, wherein said host cell lacks a fucosyltransferase such that the anti-CD30 antibody expressed by said host cell lacks fucose residues. Preferably, the immunoglobulin heavy and light chain genes are human immunoglobulin heavy and light chain genes. Preferably, the fucosyltransferase is FUT8. Preferably, the host cell is a CHO cell.

In another aspect, the invention provides a method of inhibiting growth of $CD30^+$ cells. The method involves contacting the cells with a defucosylated anti-CD30 antibody under conditions sufficient to induce antibody-dependent cellular cytotoxicity (ADCC) of said cells. The cells can be, for example, tumor cells. Preferably, the anti-CD30 antibody is a human antibody.

The invention also provides a method of inhibiting growth of tumor cells expressing CD30 in a subject. The method involves administering to the subject a defucosylated anti-CD30 antibody in an amount effective to inhibit growth of tumor cells expressing CD30 in the subject. Preferably, the anti-CD30 antibody is a human antibody. In preferred embodiments, the tumor cells are Hodgkin's Disease (HD) tumor cells or anaplastic large-cell lymphoma (ALCL) tumor cells.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 30) and amino acid sequence (SEQ ID NO: 1) of the heavy chain variable region of the 5F11 human monoclonal antibody. The CDR1 (SEQ ID NO: 7), CDR2 (SEQ ID NO: 10) and CDR3 (SEQ ID NO: 13) regions are delineated and the V, D and J germline derivations are indicated.

FIG. 1B shows the nucleotide sequence (SEQ ID NO: 33) and amino acid sequence (SEQ ID NO: 4) of the light chain variable region of the 5F11 human monoclonal antibody. The CDR1 (SEQ ID NO: 16), CDR2 (SEQ ID NO: 19) and CDR3 (SEQ ID NO: 22) regions are delineated and the V and J germline derivations are indicated.

FIG. 2A shows the nucleotide sequence (SEQ ID NO: 31) and amino acid sequence (SEQ ID NO: 2) of the heavy chain variable region of the 17G1 human monoclonal antibody. The CDR1 (SEQ ID NO: 8), CDR2 (SEQ ID NO: 11) and CDR3 (SEQ ID NO: 14) regions are delineated and the V and J germline derivations are indicated.

FIG. 2B shows the nucleotide sequence (SEQ ID NO: 34) and amino acid sequence (SEQ ID NO: 5) of the light chain variable region of the 17G1 human monoclonal antibody. The CDR1 (SEQ ID NO: 17), CDR2 (SEQ ID NO: 20) and CDR3 (SEQ ID NO: 23) regions are delineated and the V and J germline derivations are indicated.

FIG. 3A shows the nucleotide sequence (SEQ ID NO: 32) and amino acid sequence (SEQ ID NO: 3) of the heavy chain variable region of the 2H9 human monoclonal antibody. The CDR1 (SEQ ID NO: 9), CDR2 (SEQ ID NO: 12) and CDR3 (SEQ ID NO: 15) regions are delineated and the V, D, and J germline derivations are indicated.

FIG. 3B shows the nucleotide sequence (SEQ ID NO: 35) and amino acid sequence (SEQ ID NO: 6) of the light chain variable region of the 2H9 human monoclonal antibody. The CDR1 (SEQ ID NO: 18), CDR2 (SEQ ID NO: 21) and CDR3 (SEQ ID NO: 24) regions are delineated and the V and J germline derivations are indicated.

FIGS. 8A-8B show the amino acid sequences of the human germlines $V_H$ 3-11, $V_K$ L15, $V_K$ A27, and $V_K$ L6 (SEQ ID NOs:25-29, respectively), the CDRs are delineated.

FIG. 10 is a graph showing the cytotoxic cell killing activity of the fucosylated and defucosylated forms of 5F11 in the presence of mouse (left panel) or human (right panel) effector cells.

FIG. 11 is a graph showing an ADCC assay using cynomolgus blood.

DETAILED DESCRIPTION OF THE INVENTION

Figure 4:
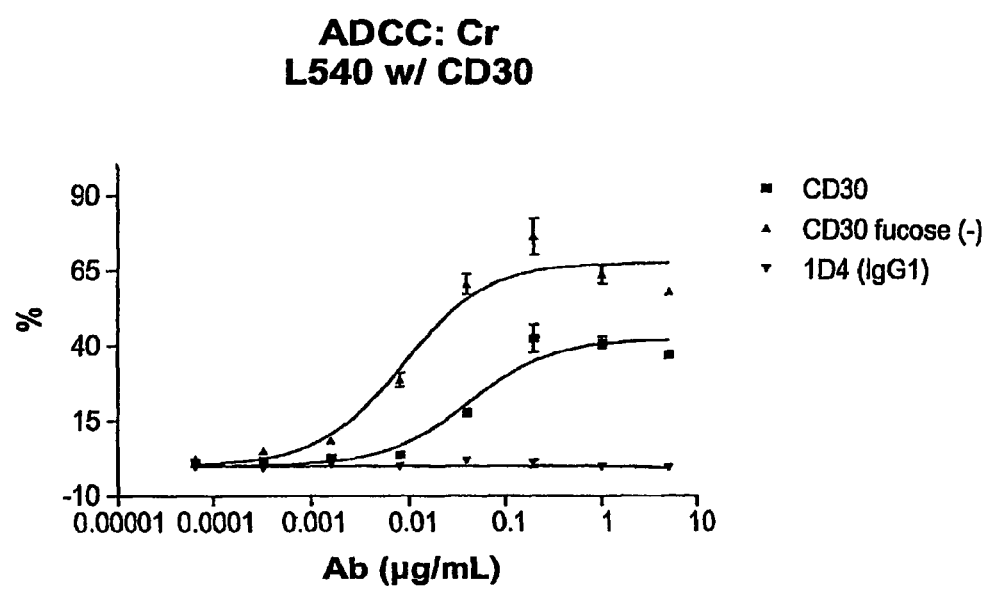
FIG. 4 is a graph showing the cytotoxic cell killing activity of the fucosylated and defucosylated forms of 5F11 on the L540 human Hodgkin's lymphoma cell line, as compared to an isotype-matched control antibody (1D4).
Figure 5:
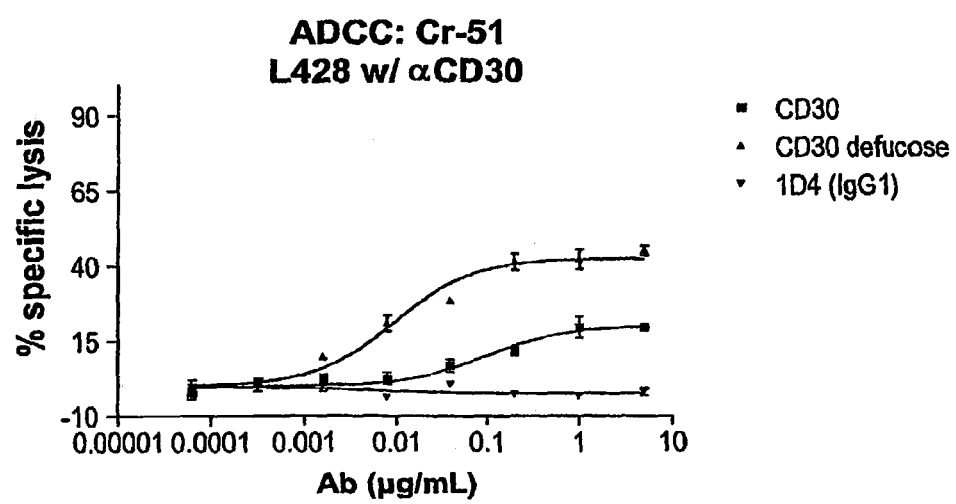
FIG. 5 is a graph showing the cytotoxic cell killing activity of the fucosylated and defucosylated forms of 5F11 on the L428 human Hodgkin's lymphoma cell line, as compared to an isotype-matched control antibody (1D4).
Figure 6:
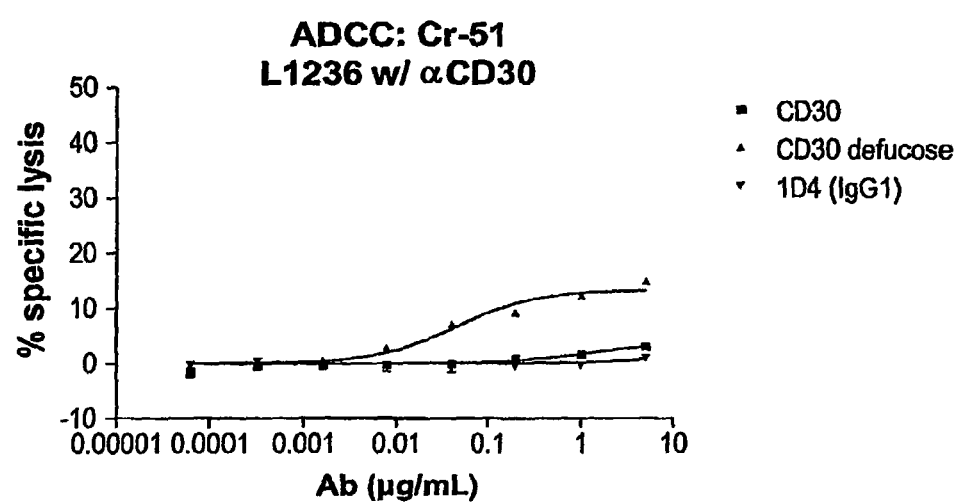
FIG. 6 is a graph showing the cytotoxic cell killing activity of the fucosylated and defucosylated forms of 5F11 on the L1236 human Hodgkin's lymphoma cell line, as compared to an isotype-matched control antibody (1D4).
Figure 7:
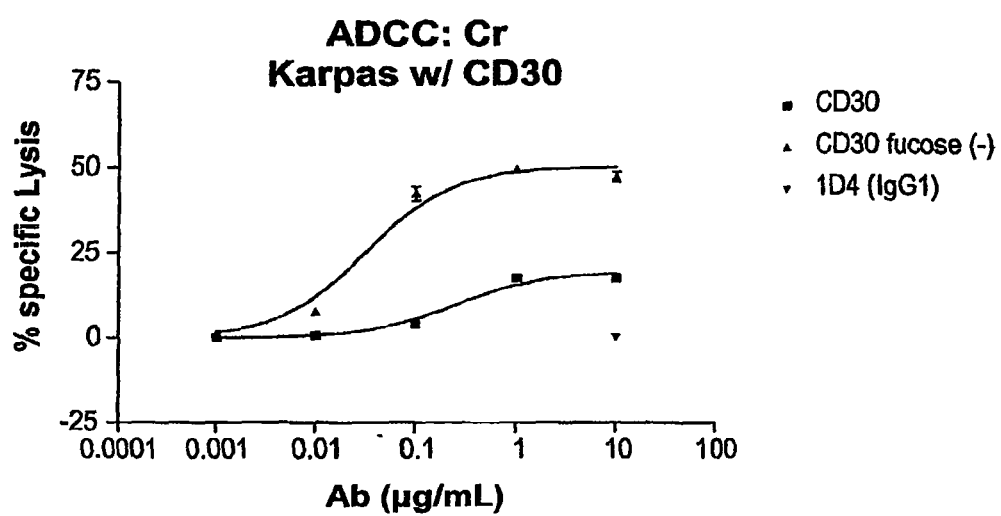
FIG. 7 is a graph showing the cytotoxic cell killing activity of the fucosylated and defucosylated forms of 5F11 on the Karpas human T cell lymphoma cell line, as compared to an isotype-matched control antibody (1D4).

The present invention provides antibody compositions and improved associated with CD30 and/or CD30 expressing cells. The antibodies of the invention lack fucosyl residues on the antibody carbohydrate chains. Furthermore, the antibodies exhibit enhanced antibody directed cellular cytotoxic (ADCC) killing of CD30+ cells. In a particular embodiment, the antibody of the current invention is capable of killing CD30+ cells under conditions in which the fucosylated form of the antibody would not effectively kill CD30+ cells. In another embodiment, the antibody of the current invention enhances killing of CD30+ cells compared to the fucosylated form of the antibody. In one embodiment, the antibodies of the present invention are fully human antibodies and are particularly useful for the therapeutic treatment in humans of disorders associated with CD30 expressing cells. Methods of using anti-CD30 antibodies lacking fucosyl residues for therapeutic treatment (e.g., to treat and/or prevent diseases associated with expression of CD30) are also encompassed by the invention.

In order that the present invention may be more readily understood, certain terms will be defined as follows. Additional definitions are set forth throughout the Detailed Description.

The terms "CD30" and "CD30 antigen" are used interchangeably herein, and include any variants, isoforms and species homologs of human CD30 which are naturally expressed by cells. The complete amino acid sequence of human CD30 protein has the Genbank accession number NP_001234. The complete cDNA sequence encoding the human CD30 protein has the Genbank accession number NM_001243.

As used herein, the terms "antibody that lacks fucose residues" and "defucosylated antibody" are used interchangeably and are intended to refer to an antibody in which the carbohydrate portion of the antibody does not contain a fucosyl residue or from which the fucosyl residue has been removed.

An antibody that lacks fucose residues can be generated, for example, by expression of the antibody in a cell or expression system that minimizes or does not attach fucosyl residues to the antibody carbohydrate chain, or by chemical modification of the antibody to remove fucosyl residues from the carbohydrate chain (e.g., treatment of the antibody with a fucosidase). As such, the terms "lacks fucose residues" and "defucosylated" are not intended to be limited by the mechanism by which the antibody with altered carbohydrate structure is prepared.

As used herein, the term "antibody expressing fucose residues" and "fucosylated antibody" are used interchangeably and are intended to refer to an antibody in which the carbohydrate portion of the antibody contains fucose.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes and macrophages, which express FcR are involved in specific killing of target cells and presenting antigens to other components of the immune system, or binding to cells that present antigens. In other embodiments, an effector cell can phagocytose a target antigen or target cell. The expression of a particular FcR on an effector cell can be regulated by humoral factors such as cytokines. For example, expression of FcαRI has been found to be up-regulated by G-CSF or GM-CSF. This enhanced expression increases the effector function of FcαRI-bearing cells against targets. An effector cell can phagocytose or lyse a target antigen or a target cell.

"Target cell" refers to any cell or pathogen whose elimination would be beneficial in a subject (e.g., a human or animal) and that can be targeted by a composition (e.g., antibody) of the invention. For example, the target cell can be a cell expressing or overexpressing CD30.

The term "antibody-dependent cellular cytotoxicity" or "ADCC" refers to a cell-mediated cytotoxic reaction in which a CD30+ target cell with bound anti-CD30 antibody is recognized by an effector cell bearing Fc receptors and is subsequently lysed without requiring the involvement of complement.

As used herein, the term "enhances ADCC" (e.g., referring to cells) is intended to include any measurable increase in cell lysis when contacted with an anti-CD30 antibody lacking fucosyl residues as compared to the cell killing of the same cell in contact with a fucosylated anti-CD30 antibody in the presence of effector cells (for example, at a ratio of target cells:effector cells of 1:50), e.g., an increase in cell lysis by at least about 10%, 20%, 30%, 40%, 50%, 60%, 70%, 80%, 90%, 100%, 150%, 200%, 250%, 300%, or 325%.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CD30). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to refer to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. The term "human monoclonal antibody", as used herein, also includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody," as used herein, is intended to refer to an antibody which is substantially free of other antibodies having different antigenic specificities (e.g., an isolated antibody that specifically binds to CD30 is substantially free of antibodies that specifically bind antigens other than CD30). An isolated antibody that specifically binds to an epitope, isoform or variant of human CD30 may, however, have cross-reactivity to other related antigens, e.g., from other species (e.g., CD30 species homologs). Moreover, an isolated antibody may be substantially free of other cellular material and/or chemicals. In one embodiment of the invention, a combination of "isolated" monoclonal antibodies having different specificities are combined in a well defined composition.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" means a protein determinant capable of specific binding to, or specific binding by, an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, "isotype" refers to the antibody class (e.g., IgM or IgG1) that is encoded by heavy chain constant region genes.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells, transfectomas, and lymphocytic cells.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

The terms "transgenic, nonhuman animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD30 antibodies when immunized with CD30 antigen and/or cells expressing CD30. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to CD30 (e.g., IgG, IgA and/or IgE) by undergoing V-D-J recombination and isotype switching.

Various aspects of the invention are described in further detail in the following subsections.

Anti-CD30 Antibodies Lacking Fucose Residues and Having Enhanced ADCC Activity

The present invention relates to a defucosylated anti-CD30 antibody with enhanced antibody directed cellular cytotoxicity (ADCC) against cells expressing CD30 as compared to the fucosylated form of the antibody. In a preferred embodiment, a defucosylated antibody of the invention induces ADCC of L1236 cells in vitro wherein the fucosylated form of the antibody does not induce ADCC, under conditions of an antibody concentration of 0.1 µg/ml and a target cell to effector cell ratio of 1:50. In another preferred embodiment, a defucosylated antibody of the invention enhances ADCC of L540, L428 and Karpas cells in vitro compared to the fucosylated form of the antibody, under conditions of an antibody concentration of 0.1 µg/ml and a target cell to effector cell ratio of 1:50.

The increased ADCC activity of a defucosylated antibody of the invention can be quantitated, for example, as an increase in percent cell lysis, as compared to the fucosylated form of the antibody, when ADCC activity is measured under the same conditions for the defucosylated and fucosylated forms (e.g., same antibody concentrations and same target to effector cell ratios). Preferably, a defucosylated anti-CD30 antibody of the invention increases the percent lysis of CD30+ cells as compared to the fucosylated form of the antibody at least 1.25 fold (i.e., the ratio of the % lysis of the defucosylated form to the fucosylated form is at least 1.25), more preferably at least 2 fold, even more preferably at least 2.5 fold and even more preferably at least 3 fold. In various embodiments, the defucosylated form of the antibody increases percent lysis of CD30+ cells as compared to the fucosylated form of the antibody from 1.25 to 3.25 fold, preferably 1.5 to 3.25 fold, even more preferably 1.61 to 3.25 fold, even more preferably 2.15 to 3.25 fold, and even more preferably 2.63 to 3.25 fold, preferably under conditions where the antibody is at a concentration of 25 µg/ml and the target to effector cell ratio is 1:50.

Additionally or alternatively, the increased ADCC activity of a defucosylated antibody of the invention can be quantitated, for example, as an increased potency as measured by a decrease in the $EC_{50}$ value for the defucosylated form, as compared to the fucosylated form. This can be quantitated by the ratio of the $EC_{50}$ for the fucosylated form to the defucosylated form. Preferably, the $EC_{50}$ ratio of the fucosylated form to the defucosylated form for ADCC of CD30+ cells is at least 3 (i.e., the $EC_{50}$ of the defucosylated form is 3-fold lower than the $EC_{50}$ of the fucosylated form), more preferably, at least 4, even more preferably at least 5, at least 7, at least 10, at least 15 or at least 20. In various embodiments, the $EC_{50}$ ratio of the fucosylated form to the defucosylated form for ADCC of CD30+ cells is from 2 to 27.1, more preferably from 4 to 27.1, even more preferably from 4.7 to 27.1, even more preferably from 7.8 to 27.1, and even more preferably from 11.1 to 27.1. Preferably, the EC50 values are determined in ADCC assays that use a target to effector cell ratio of 1:50 and antibody concentrations from 0.0001 µg/ml to 10 µg/ml or higher.

Examples of CD30+ cell lines that can be used in the ADCC assays of the invention and against which a defucosylated antibody of the invention exhibits enhanced ADCC activity, as compared to the fucosylated form of the antibody, include L540 cells (human Hodgkin's lymphoma; DSMZ Deposit No. ACC 72), L428 cells (human Hodgkin's lymphoma; DSMZ Deposit No. ACC 197), L1236 cells (human Hodgkin's lymphoma; DSMZ Deposit No. ACC 530), and Karpas cells (human T cell lymphoma; DSMZ Deposit No. ACC 31). The enhanced ADCC effect by defucosylated anti-CD30 antibodies may result in ADCC activity on CD30+ cells at antibody concentrations where ADCC would not be observed with the fucosylated form of the antibody. For example, in an in vitro ADCC assay with a target:effector cell ratio of 1:50, ADCC due to a defucosylated anti-CD30 antibody is observed with the CD30+ cell line L1236 at concentrations as low as 0.005 µg/ml, whereas no ADCC activity is detected with the fucosylated anti-CD30 antibody at concentrations as high as 0.1 µg/ml.

Defucosylation of Anti-CD30 Antibodies

Anti-CD30 antibodies (e.g., murine, chimeric, humanized and human antibodies) are known in the art, and may be used in the present invention. The anti-CD30 antibody of the present invention is modified such that the antibody is lacking in fucosyl residues. An antibody can be made that is lacking in fucosyl residues by one of a variety of methods. For example, the antibody can be expressed, using recombinant DNA technology, in a cell with an altered glycosylation mechanism such that addition of fucosyl residues to carbohydrate chains is inhibited. Additionally or alternatively, an antibody can be defucosylated through chemical removal of the fucosyl residue.

In one embodiment, the antibody is expressed in a cell that is lacking in a fucosyltransferase enzyme such that the cell line produces proteins lacking fucose in their carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which naturally have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)—N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

In another embodiment, an anti-CD30 antibody is expressed and the fucosyl residue(s) is cleaved using a fucosidase enzyme. For example, the fucosidase alpha-L-fucosidase removes fucosyl residues from antibodies (Tarentino, A. L. et al. (1975) *Biochem.* 14:5516-23).

Additionally, in other embodiments, other forms of glycosylation of an antibody are also modified. For example, an aglycoslated antibody can be made (i.e., the antibody lacks glycosylation). Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Characterization of Absence of Fucosyl Residues on Anti-CD30 Antibodies

Antibodies of the invention lack fucosyl residues, for example in the Fc portion carbohydrate chain. Antibodies can be tested for the absence of fucosyl residues using standard techniques known in the art, such as APTS capillary electrophoresis laser induced fluorescence. Briefly, the N-linked oligosaccharides of the purified anti-CD30 antibody can be released by adding the peptide N-glycanase (Prozyme) and incubating overnight. The carbohydrates are resuspended and derivatized with 8-aminopyrene-1,3,6-trisulfonate (APTS) under mild reductive amination conditions in which desialylation and loss of fucosyl residues is minimized. The reaction adducts are analyzed by capillary electrophoresis with a laser-induced fluorescence detector (Beckman Coulter). An absence of fucose can be observed by a shift in the electrophoresis compared to the same antibody containing fucose. Another technique for testing the absence of fucose on anti-CD30 antibodies is a monosaccharide analysis using HPLC. Suitable assays to determine CD30 binding are further described in the Examples.

Characterization of Antibody Dependent Cell Killing of CD30+ Cells

Defucosylated anti-CD30 antibodies can be tested for their ability to mediate phagocytosis and killing of cells expressing CD30. In one embodiment, a defucosylated anti-CD30 antibody enhances killing of cells expressing CD30 in comparison to the same antibody containing fucose when compared at the same concentration. In another embodiment, a defucosylated anti-CD30 antibody induces killing of cells expressing CD30 where the same antibody containing fucose does not induce cell killing at the same concentration.

The ADCC activity of a monoclonal antibody can be tested in established in vitro assays. As an example, a chromium release ADCC assay may be used. Briefly, peripheral blood mononuclear cells (PBMCs), or other effector cells, from healthy donors can be purified by Ficoll Hypaque density centrifugation, followed by lysis of contaminating erythrocytes. Washed PBMCs can be suspended in RPMI supplemented with 10% heat-inactivated fetal calf serum and mixed with $^{51}$Cr labeled cells expressing CD30, at various ratios of effector cells to tumor cells (effector cells:tumor cells). Anti-CD30 antibody can then be added at various concentrations. An isotype matched antibody can be used as a negative control. Assays can be carried out for 4-18 hours at 37° C. Samples can be assayed for cytolysis by measuring $^{51}$Cr release into the culture supernatant. Anti-CD30 monoclonal can also be tested in combinations with each other to determine whether cytolysis is enhanced with multiple monoclonal antibodies.

An alternative assay that can be used to test for anti-CD30 antibody ability to mediate phagocytosis and killing of cells expressing CD30 is a time resolved fluorometry assay. Briefly, CD30 expressing cells are loaded with an acetoxymethyl ester of fluorescence enhancing ligand (BATDA), which penetrates cell membranes. Inside the cell, the ester bonds are hydrolized and the compound can no longer pass the cell membrane. Anti-CD30 antibody can then be added at various concentrations. Following cytolysis, an europeum solution (Perkin Elmer) is added and any free ligand binds the europeum to form a highly fluorescent and stable chelate (EuTDA) that can be read on a microplate reader (Perkin Elmer). The measured signal correlates with the amount of lysed cells.

Anti-CD30 antibodies also can be tested in an in vivo model (e.g., in mice) to determine their efficacy in mediating phagocytosis and killing of cells expressing CD30, e.g., tumor cells. These antibodies can be selected, for example, based on the following criteria, which are not intended to be exclusive:

1) binding to live cells expressing CD30;
2) high affinity of binding to CD30;
3) binding to a unique epitope on CD30 (to eliminate the possibility that monoclonal antibodies with complimentary activities when used in combination would compete for binding to the same epitope);
4) opsonization of cells expressing CD30;
5) mediation in vitro of growth inhibition, phagocytosis and/or killing of cells expressing CD30 in the presence of human effector cells.

Preferred monoclonal antibodies of the invention meet one or more of these criteria. In a particular embodiment, the monoclonal antibodies are used in combination, e.g., as a pharmaceutical composition comprising two or more anti-CD30 monoclonal antibodies or fragments thereof. For example, anti-CD30 monoclonal antibodies having different, but complementary activities can be combined in a single therapy to achieve a desired therapeutic or diagnostic effect.

An illustration of this would be a composition containing an anti-CD30 monoclonal antibody that mediates highly effective killing of target cells in the presence of effector cells, combined with another anti-CD30 monoclonal antibody that inhibits the growth of cells expressing CD30.

Characterization of Binding to CD30

Antibodies of the invention can be tested for binding to CD30 by, for example, standard assays known in the art, such as ELISA, FACS analysis and/or Biacore analysis. In a typical ELISA assay, briefly, microtiter plates are coated with purified CD30 at 0.25 μg/ml in PBS, and then blocked with 5% bovine serum albumin in PBS. Dilutions of antibody are added to each well and incubated for 1-2 hours at 37° C. The plates are washed with PBS/Tween and then incubated with secondary reagent (e.g., for human antibodies or a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650.

In order to demonstrate binding of monoclonal antibodies to live cells expressing the CD30, flow cytometry can be used. In a typical (but non-limiting) example of a flow cytometry protocol, cell lines expressing CD30 (grown under standard growth conditions) are mixed with various concentrations of monoclonal antibodies in PBS containing 0.1% BSA and 20% mouse serum, and incubated at 37° C. for 1 hour. After washing, the cells are reacted with Fluorescein-labeled secondary antibody (e.g., anti-human IgG antibody) under the same conditions as the primary antibody staining. The samples can be analyzed by a FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD30 antibodies can be further tested for reactivity with CD30 antigen by Western blotting. For example, cell extracts from cells expressing CD30 can be prepared and subjected to sodium dodecyl sulfate (SDS) polyacrylamide gel electrophoresis. After electrophoresis, the separated antigens are transferred to nitrocellulose membranes, blocked with 20% mouse serum, and probed with the monoclonal antibodies to be tested. Antibody binding can be detected using anti-species specific secondary antibody linked to alkaline phosphatase and developed with BCIP/NBT substrate tablets (Sigma Chem. Co., St. Louis, Mo.). Other techniques for evaluating the binding ability of antibodies towards CD30 are known in the art, including RIAs and Biacore analysis. Suitable assays to determine CD30 binding are described in detail in the Examples.

Chimeric or Humanized Anti-CD30 Antibodies

In certain embodiments, a defucosylated anti-CD30 antibody of the invention is a chimeric or humanized antibody. Such antibodies can be prepared using mouse anti-CD30 antibodies that are available in the art and established procedures for converting a mouse antibody to a chimeric or humanized antibody. Non-limiting examples of such mouse anti-CD30 antibodies include the AC10, HeFi-1, Ber-H2, Ki-1, Ki-4, HRS-3, Irac, HRS-4, M44, M67 and Ber-H8 monoclonal antibodies. Moreover, humanized anti-CD30 antibodies are described in PCT Publication WO 02/4661.

Human Monoclonal Anti-CD30 Antibodies

Preferred antibodies of the invention include human anti-CD30 monoclonal antibodies. Examples of human anti-CD30 monoclonal antibodies include the 5F11, 17G1, and 2H9 antibodies, isolated and structurally characterized as originally described in PCT Publication WO 03/059282. The $V_H$ amino acid sequences of 5F11, 17G1, and 2H9 are shown in SEQ ID NOs: 1, 2, and 3, respectively. The $V_L$ amino acid sequences of 5F11, 17G1, and 2H9 are shown in SEQ ID NOs: 4, 5, and 6, respectively.

Given that each of these antibodies can bind to CD30, the $V_H$ and $V_L$ sequences can be "mixed and matched" to create other anti-CD30 binding molecules of the invention. CD30 binding of such "mixed and matched" antibodies can be tested using the binding assays well known in the art, such as FACS analysis and ELISA assays. Preferably, when $V_H$ and $V_L$ chains are mixed and matched, a $V_H$ sequence from a particular $V_H/V_L$ pairing is replaced with a structurally similar $V_H$ sequence Likewise, preferably a $V_L$ sequence from a particular $V_H/V_L$ pairing is replaced with a structurally similar $V_L$ sequence. For example, the $V_H$ sequences of 5F11 and 2H9 are particularly amenable for mixing and matching, since these antibodies use $V_H$ sequences derived from the same germline sequence ($V_H$ 4-34) and thus they exhibit structural similarity.

In particular embodiments, the invention provides a defucosylated monoclonal antibody, or antigen binding portion thereof, comprising:

(a) a heavy chain variable region comprising an amino acid sequence selected from the group consisting of SEQ ID NOs: 1, 2, and 3; and (b) a light chain variable region comprising an amino acid sequence selected from the group consisting of SEQ ID NO: 4, 5, and 6;

wherein the antibody specifically binds human CD30.

Preferred heavy and light chain combinations include:

(a) a heavy chain variable region comprising the amino acid sequence of SEQ ID NO: 1; and (b) a light chain variable region comprising the amino acid sequence of SEQ ID NO: 4; or (a) a heavy chain variable region comprising the amino acid sequence of SEQ ID NO: 2; and (b) a light chain variable region comprising the amino acid sequence of SEQ ID NO: 5; or (a) a heavy chain variable region comprising the amino acid sequence of SEQ ID NO: 3; and (b) a light chain variable region comprising the amino acid sequence of SEQ ID NO: 6.

In another aspect, the invention provides defucosylated antibodies that comprise the heavy chain and light chain CDR1s, CDR2s and CDR3s of 5F11, 17G1, and 2H9, or combinations thereof. The amino acid sequences of the $V_H$ CDR1s of 5F11, 17G1, and 2H9 are shown in SEQ ID NOs: 7, 8, and 9, respectively. The amino acid sequences of the $V_H$ CDR2s of 5F11, 17G1, and 2H9 are shown in SEQ ID NOs: 10, 11, and 12, respectively. The amino acid sequences of the $V_H$ CDR3s of 5F11, 17G1, and 2H9 are shown in SEQ ID NOs: 13, 14, and 15, respectively. The amino acid sequences of the $V_K$ CDR1s of 5F11, 17G1, and 2H9 are shown in SEQ ID NOs: 16, 17, and 18, respectively. The amino acid sequences of the $V_K$ CDR2s of 5F11, 17G1, and 2H9 are shown in SEQ ID NOs: 19, 20, and 21, respectively. The amino acid sequences of the $V_K$ CDR3s of 5F11, 17G1, and 2H9 are shown in SEQ ID NOs: 22, 23, and 24, respectively. The CDR regions are delineated using the Kabat system (Kabat, E. A., et al. (1991) *Sequences of Proteins of Immunological Interest*, Fifth Edition, U.S. Department of Health and Human Services, NIH Publication No. 91-3242).

Given that each of these antibodies can bind to CD30 and that antigen-binding specificity is provided primarily by the CDR1, 2 and 3 regions, the $V_H$ CDR1, 2 and 3 sequences and $V_k$ CDR1, 2 and 3 sequences can be "mixed and matched"

(i.e., CDRs from different antibodies can be mixed and match, although each antibody must contain a $V_H$ CDR1, 2 and 3 and a $V_k$ CDR1, 2 and 3) to create other anti-CD30 binding molecules of the invention. CD30 binding of such "mixed and matched" antibodies can be tested using binding assays know in the art, for example, FACS analysis and ELISA assays. Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 5F11, 17G1, and 2H9.

Accordingly, in another aspect, the invention provides a defucosylated monoclonal antibody, or antigen binding portion thereof comprising:

(a) a heavy chain variable region CDR1 comprising an amino acid sequence selected from the group consisting of SEQ ID NOs: 7, 8, and 9;

(b) a heavy chain variable region CDR2 comprising an amino acid sequence selected from the group consisting of SEQ ID NOs: 10, 11, and 12;

(c) a heavy chain variable region CDR3 comprising an amino acid sequence selected from the group consisting of SEQ ID NOs: 13, 14, and 15;

(d) a light chain variable region CDR1 comprising an amino acid sequence selected from the group consisting of SEQ ID NOs: 16, 17, and 18;

(e) a light chain variable region CDR2 comprising an amino acid sequence selected from the group consisting of SEQ ID NOs: 19, 20, and 21; and (f) a light chain variable region CDR3 comprising an amino acid sequence selected from the group consisting of SEQ ID NOs: 22, 23, and 24;

wherein the antibody specifically binds CD30.

In a preferred embodiment, the antibody comprises:

(a) a heavy chain variable region CDR1 comprising SEQ ID NO: 7;

(b) a heavy chain variable region CDR2 comprising SEQ ID NO: 10;

(c) a heavy chain variable region CDR3 comprising SEQ ID NO: 13;

(d) a light chain variable region CDR1 comprising SEQ ID NO: 16;

(e) a light chain variable region CDR2 comprising SEQ ID NO: 19; and (f) a light chain variable region CDR3 comprising SEQ ID NO: 22.

In another preferred embodiment, the antibody comprises:

(a) a heavy chain variable region CDR1 comprising SEQ ID NO: 8;

(b) a heavy chain variable region CDR2 comprising SEQ ID NO: 11;

(c) a heavy chain variable region CDR3 comprising SEQ ID NO: 14;

(d) a light chain variable region CDR1 comprising SEQ ID NO: 17;

(e) a light chain variable region CDR2 comprising SEQ ID NO: 20; and (f) a light chain variable region CDR3 comprising SEQ ID NO: 24.

In another preferred embodiment, the antibody comprises:

(a) a heavy chain variable region CDR1 comprising SEQ ID NO: 9;

(b) a heavy chain variable region CDR2 comprising SEQ ID NO: 12;

(c) a heavy chain variable region CDR3 comprising SEQ ID NO: 15;

(d) a light chain variable region CDR1 comprising SEQ ID NO: 18;

(e) a light chain variable region CDR2 comprising SEQ ID NO: 21; and (f) a light chain variable region CDR3 comprising SEQ ID NO: 24.

Antibodies Having Particular Germline Sequences

In certain embodiments, a defucosylated antibody of the invention comprises a heavy chain variable region from a particular germline heavy chain immunoglobulin gene and/or a light chain variable region from a particular germline light chain immunoglobulin gene.

For example, in a preferred embodiment, the invention provides a defucosylated monoclonal antibody, or an antigen-binding portion thereof, comprising a heavy chain variable region that is the product of or derived from a human $V_H$ 4-34 gene, wherein the antibody specifically binds to human CD30. In another preferred embodiment, the invention provides a defucosylated monoclonal antibody, or an antigen-binding portion thereof, comprising a heavy chain variable region that is the product of or derived from a human $V_H$ 3-07 gene, wherein the antibody specifically binds CD30. In another preferred embodiment, the invention provides a defucosylated monoclonal antibody, or an antigen-binding portion thereof, comprising a light chain variable region that is the product of or derived from a human $V_K$ L15 gene, wherein the antibody specifically binds to human CD30. In another preferred embodiment, the invention provides a defucosylated monoclonal antibody, or an antigen-binding portion thereof, comprising a light chain variable region that is the product of or derived from a human $V_K$ A27 gene, wherein the antibody specifically binds to human CD30. In another preferred embodiment, the invention provides a defucosylated monoclonal antibody, or an antigen-binding portion thereof, comprising a light chain variable region that is the product of or derived from a human $V_K$ L6 gene, wherein the antibody specifically binds to human CD30.

In yet another preferred embodiment, the invention provides a defucosylated monoclonal antibody, or an antigen-binding portion thereof, wherein the antibody:

(a) comprises a heavy chain variable region that is the product of or derived from a human $V_H$ 4-34 or 3-07 gene (which encodes the amino acid sequence set forth in SEQ ID NOs: 25 and 26, respectively);

(b) comprises a light chain variable region that is the product of or derived from a human $V_k$ L15, A27, or L6 gene (which encode the amino acid sequences set forth in SEQ ID NOs: 27, 28, and 29, respectively); and (c) specifically binds to human CD30.

A preferred $V_H$ and $V_k$ germline combination is $V_H$ 4-34 and $V_k$ L15. An example of an antibody having $V_H$ and $V_K$ of $V_H$ 4-34 and $V_k$ L15, respectively, is the 5F11 antibody. Another preferred $V_H$ and $V_k$ germline combination is $V_H$ 3-07 and $V_k$ A27. An example of an antibody having $V_H$ and $V_k$ of $V_H$ 3-07 and Vk A27, respectively, is the 17G1 antibody. Another preferred $V_H$ and $V_k$ germline combination is $V_H$ 4-34 and $V_k$ L6. An example of an antibody having $V_H$ and $V_k$ of $V_H$ 4-34 and $V_k$ L6, respectively, is the 2H9 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins (eg., using the Vbase database) and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, a defucosylated antibody of the invention comprises heavy and light chain variable regions comprising amino acid sequences that are homologous to the amino acid sequences of the preferred antibodies described herein, and wherein the antibodies retain the desired functional properties of the anti-CD30 antibodies of the invention.

For example, the invention provides a defucosylated monoclonal antibody, or antigen binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 1, 2, and 3;
(b) the light chain variable region comprises an amino acid sequence that is at least 80% homologous to an amino acid sequence selected from the group consisting of SEQ ID NOs: 4, 5, and 6; and
(c) the antibody specifically binds to human CD30.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of one or more nucleic acid molecules encoding SEQ ID NOs: 1-6, followed by testing of the encoded altered antibody for retained function (i.e., binding to CD30) using the binding assays described herein.

Nucleic acid molecules encoding SEQ ID NOs: 1-6 are shown in SEQ ID NOs: 30-35.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, a defucosylated antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 5F11, 17G1, and 2H9), or conservative modifications thereof, and wherein the antibodies retain the desired functional properties of the anti-CD30 antibodies of the invention. Accordingly, the invention provides a defucosylated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:
  (a) the heavy chain variable region CDR3 sequence comprises the amino acid sequence of SEQ ID NO: 9, 12, or 15, and conservative modifications thereof;
  (b) the light chain variable region CDR3 sequence comprises the amino acid sequence of SEQ ID NO: 18, 21, or 24, and conservative modifications thereof; and
  (c) the antibody specifically binds to human CD30.

In a preferred embodiment, the heavy chain variable region CDR2 sequence comprises the amino acid sequence of SEQ ID NO: 8, 11, or 14, and conservative modifications thereof; and the light chain variable region CDR2 sequence comprises the amino acid sequence of SEQ ID NO: 17, 20, or 23, and conservative modifications thereof. In another preferred embodiment, the heavy chain variable region CDR1 sequence comprises the amino acid sequence of SEQ ID NO: 7, 10, or 13, and conservative modifications thereof; and the light chain variable region CDR1 sequence comprises the amino acid sequence of SEQ ID NO: 16, 19, or 22, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (i) through (iv) above) using the functional assays described herein.

Alternatively, in another embodiment, mutations can be introduced randomly along all or part of an anti-CD30 antibody coding sequence, such as by saturation mutagenesis, and the resulting modified anti-CD30 antibodies can be screened for binding activity.

Antibodies that Bind to the Same Epitope as Anti-CD30 Antibodies of the Invention In another embodiment, the invention provides defucosylated antibodies that bind to the same epitope as do the various anti-CD30 antibodies of the invention provided herein, such as other human antibodies that bind to the same epitope as the 5F11, 17G1 or 2H9 antibodies described herein. Such additional antibodies can be identified based on their ability to cross-compete (e.g., to competitively inhibit the binding of, in a statistically significant manner) with other antibodies of the invention, such as 5F11, 17G1 or 2H9, in standard CD30 binding assays. The ability of a test antibody to inhibit the binding of, e.g., 5F11, 17G1 or 2H9 to human CD30 demonstrates that the test antibody can compete with that antibody for binding to human CD30; such an antibody may, according to non-limiting theory, bind to the same or a related (e.g., a structurally similar or spatially proximal) epitope on human CD30 as the antibody with which it competes. In a preferred embodiment, the defucosylated antibody that binds to the same epitope on human CD30 as 5F11, 17G1 or 2H9 is a human monoclonal antibody. Such human monoclonal antibodies can be prepared and isolated as described in PCT Publication WO 03/059282.

Engineered and Modified Antibodies

A defucosylated antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more amino acid residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to a defucosylated monoclonal antibody, or antigen binding portion thereof, comprising a heavy chain variable region comprising CDR1, CDR2, and CDR3 sequences comprising an amino acid sequence selected from the group consisting of SEQ ID NOs: 7, 8, and 9, SEQ ID NOs: 10, 11, and 12, and SEQ ID NOs: 13, 14, and 15, respectively, and a light chain variable region comprising an amino acid sequence selected from the group consisting of SEQ ID NOs: 16, 17, and 18, SEQ ID NOs: 19, 20, and 21 and SEQ ID NOs: 22, 23, and 24, respectively. Thus, such antibodies contain the $V_H$ and $V_L$ CDR sequences of monoclonal antibodies 5F11, 17G1, or 2H9 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 4-34 or 3-07 sequences (SEQ ID NO: 25 or 26) and/or the $V_k$ L15, A27 or L6 framework sequence (SEQ ID NO: 27, 28, or 29) used by preferred monoclonal antibodies of the invention. The $V_H$ CDR1, 2 and 3 sequences, and the $V_K$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides defucosylated anti-CD30 monoclonal antibodies, or antigen binding portions thereof, comprising a heavy chain variable region comprising: (a) a $V_H$ CDR1 region comprising an amino acid sequence selected from the group consisting of SEQ ID NO: 7, 8, and 9, or an amino acid sequence having one, two, three, four or five amino acid substitutions, deletions or additions as compared to an amino acid sequence selected from the group consisting of SEQ ID NO: 7, 8, and 9; (b) a $V_H$ CDR2 region comprising an amino acid sequence selected from the group consisting of SEQ ID NO: 10, 11, and 12, or an amino acid sequence having one, two, three, four or five amino acid substitutions, deletions or additions as compared to an amino acid sequence selected from the group consisting of SEQ ID NO: 10, 11, and 12; (c) a $V_H$ CDR3 region comprising an amino acid sequence selected from the group consisting of SEQ ID NO: 13, 14, and 15, or an amino acid sequence having one, two, three, four or five amino acid substitutions, deletions or additions as compared to an amino acid sequence selected from the group consisting of SEQ ID NO: 13, 14, and 15; (d) a $V_K$ CDR1 region comprising an amino acid sequence selected from the group consisting of SEQ ID NO: 16, 17 and 18, or an amino acid sequence having one, two, three, four or five amino acid substitutions, deletions or additions as compared to an amino acid sequence selected from the group consisting of SEQ ID NO: 16, 17, and 18; (e) a $V_K$ CDR2 region comprising an amino acid sequence selected from the group consisting of SEQ ID NO: 19, 20, and 21, or an amino acid sequence having one, two, three, four or five amino acid substitutions, deletions or additions as compared to an amino acid sequence selected from the group consisting of SEQ ID NO: 19, 20, and 21; and (f) a $V_K$ CDR3 region comprising an amino acid sequence selected from the group consisting of SEQ ID NO: 22, 23, and 24, or an amino acid sequence having one, two, three, four or five amino acid substitutions, deletions or additions as compared to an amino acid sequence selected from the group consisting of SEQ ID NO: 22, 23, and 24.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 5F11, amino acid residue #83 (within FR3) of $V_H$ is an asparagine whereas this residue in the corresponding $V_H$ 4-34 germline sequence is a serine. To return the framework region sequences to their germline configuration, the somatic mutations can be "backmutated" to the germline sequence by, for example, site-directed mutagenesis or PCR-mediated mutagenesis (e.g., residue 83 of FR3 of the $V_H$ of 5F11 can be "backmutated" from asparagine to serine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody.

More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the defucosylated anti-CD30 antibodies having $V_H$ and $V_K$ sequences disclosed herein can be used to create new anti-CD30 antibodies by modifying the VH and/or $V_K$ sequences, or the constant region(s) attached thereto. Thus, in another aspect of the invention, the structural features of an anti-CD30 antibody of the invention, e.g. 5F11, 17G1, or 2H9, are used to create structurally related defucosylated anti-CD30 antibodies that retain at least one functional property of the antibodies of the invention, such as binding to human CD30. For example, one or more CDR regions of 5F11, 17G1, or 2H9, or mutations thereof, can be combined recombinantly with known framework regions and/or other CDRs to create additional, recombinantly-engineered, anti-CD30 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-CD30 antibody comprising:

(a) providing: (i) a heavy chain variable region antibody sequence comprising a CDR1 sequence selected from the group consisting of SEQ ID NOs: 7, 8, and 9, a CDR2 sequence selected from the group consisting of SEQ ID NOs: 10, 11, and 12 and/or a CDR3 sequence selected from the group consisting of SEQ ID NOs: 13, 14, and 15; and/or (ii) a light chain variable region antibody sequence comprising a CDR1 sequence selected from the group consisting of SEQ ID NOs: 16, 17, and 18, a CDR2 sequence selected from the group consisting of SEQ ID NOs: 19, 20, and 21 and/or a CDR3 sequence selected from the group consisting of SEQ ID NOs: 22, 23, and 24;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence. The altered antibody sequence so prepared can then be made in defucosylated form using the methods disclosed herein to obtain a defucosylated altered anti-CD30 antibody.

The functional properties of the altered antibodies can be assessed using standard assays available in the art and/or described herein, such as those set forth in the Examples (e.g., flow cytometry, binding assays, ADCC assays).

In certain embodiments of the methods of engineering antibodies of the invention, mutations can be introduced randomly or selectively along all or part of an anti-CD30 antibody coding sequence and the resulting modified anti-CD30 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The term "nucleic acid molecule", as used herein, is intended to include DNA molecules and RNA molecules. A nucleic acid molecule may be single-stranded or double-stranded, but preferably is double-stranded DNA. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) *Current Protocols in Molecular Biology*, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 5F11, 17G1, and 2H9 monoclonal antibodies. The DNA sequence encoding the VH sequence of 5F11 is shown in SEQ ID NO: 30. The DNA sequence encoding the VL sequence of 5F11 is shown in SEQ ID NO: 33. The DNA sequence encoding the VH sequence of 17G1 is shown in SEQ ID NO: 31. The DNA sequence encoding the VL sequence of 17G1 is shown in SEQ ID NO: 34. The DNA sequence encoding the VH sequence of 2H9 is shown in SEQ ID NO: 32. The DNA sequence encoding the VL sequence of 2H9 is shown in SEQ ID NO: 35.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In various embodiments, the antibody can be, for example, human antibodies, humanized antibodies or chimeric antibodies.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.). A variety of mouse anti-CD30 antibodies are known in the art that can be used to create chimeric or humanized anti-CD30 antibodies, for example, AC10, HeFi-1, Ber-H2, Ki-1, HRS-3, Trac, HRS-4, M44, M67, and Ber-H8.

In a preferred embodiment, the antibodies of the invention are human monoclonal antibodies. Such human monoclonal antibodies directed against CD30 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGx monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-CD30 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD30 antibodies of the invention. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-CD30 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of CD30 antigen and/or recombinant CD30, or an CD30 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of CD30 antigen can be used to immunize the human Ig mice intraperitoneally.

Detailed procedures to generate fully human monoclonal antibodies to CD30 are described in PCT Publication WO 03/059282. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retro-orbital bleeds. The plasma can be screened by ELISA (as described below), and mice with sufficient titers of anti-CD30 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3x63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of well known recombinant DNA techniques and gene transfection methods (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred host cells for expressing the recombinant antibodies of the invention include cells which modify the fucosylation of an expressed antibody. For example, the host cell may be a cell that is lacking in a fucosyltransferase enzyme such that the host cell produces proteins lacking fucose in their carbohydrates, or a host cell that expresses glycoprotein-modifying glycosyl transferases such that expressed antibodies in the host cell have increased bisecting GlcNac structures that prevents fucosylation. Other mammalian host cells for expressing the recombinant antibodies include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

In another aspect, the present invention features a defucosylated anti-CD30 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indiumin$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates of the invention. For example, a pharmaceutical composition of the invention can comprise a combination of antibodies (or immunoconjugates) that bind to different epitopes on the target antigen or that have complementary activities.

Pharmaceutical compositions of the invention also can be administered in combination therapy, i.e., combined with other agents. For example, the combination therapy can include a defucosylated anti-CD30 antibody of the present invention combined with at least one other anti-neoplastic, anti-inflammatory or immunosuppressive agent. Such therapeutic agents include, among others, steroidal and nonsteroidal anti-inflammatory drugs (NSAIDS), e.g., aspirin and other salicylates, such as ibuprofen (Motrin, Advil), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), indomethacin (Indocin), and aspirin in high doses. Other examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjuage, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for a defucosylated anti-CD30 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD30 antibody of the invention preferably results in a decrease in severity of disease symptoms, an increase in frequency and duration of disease symptom-free periods, or a prevention of impairment or disability due to the disease affliction. For example, for the treatment of cancerous tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a defucosylated antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the defucosylated antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

USES AND METHODS OF THE INVENTION

The defucosylated antibodies, antibody compositions and methods of the present invention have numerous in vitro and in vivo diagnostic and therapeutic utilities involving the diagnosis and treatment of disorders involving CD30 expression. For example, these molecules can be administered to cells in culture, e.g. in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, pigs, chickens, avians, amphibians, and reptiles. Preferred subjects include human patients having disorders characterized by CD30 expression. When antibodies to CD30 are administered together with another agent, the two can be administered in either order or simultaneously.

Suitable routes of administering the antibody compositions (e.g., antibody or immunoconjugate) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

In one embodiment, the antibodies of the invention can be initially tested for binding activity associated with therapeutic or diagnostic use in vitro. For example, compositions of the invention can be tested using ELISA and flow cytometric assays. Moreover, the activity of these molecules in triggering at least one effector-mediated effector cell activity, including inhibiting the growth of and/or killing of cells expressing CD30 can be assayed. Protocols for assaying for effector cell-mediated ADCC are described in the Examples below.

A. Detection Methods

In one embodiment, the antibodies of the invention can be used to detect levels of CD30, or levels of cells which contain CD30 on their membrane surface, which levels can then be linked to certain disease symptoms.

In a particular embodiment, the invention provides methods for detecting the presence of CD30 antigen in a sample, or measuring the amount of CD30 antigen, comprising contacting the sample, and a control sample, with a defucosylated antibody, or an antigen binding portion thereof, which specifically binds to CD30, under conditions that allow for formation of a complex between the antibody or portion thereof and CD30. The formation of a complex is then detected, wherein a difference complex formation between the sample compared to the control sample is indicative the presence of CD30 antigen in the sample. For example, standard detection methods, well-known in the art, such as ELISA and flow cytometric assays, can be performed using the compositions of the invention.

Accordingly, in one aspect, the invention further provides methods for detecting the presence of CD30 (e.g., human CD30 antigen) in a sample, or measuring the amount of CD30, comprising contacting the sample, and a control sample, with an antibody of the invention, or an antigen binding portion thereof, which specifically binds to CD30, under conditions that allow for formation of a complex between the antibody or portion thereof and CD30. The formation of a complex is then detected, wherein a difference in complex formation between the sample compared to the control sample is indicative of the presence of CD30 in the sample.

The compositions of the invention can also be used to target cells expressing CD30, for example for labeling such cells. For such use, the binding agent can be linked to a molecule that can be detected. Thus, the invention provides methods for localizing ex vivo or in vitro cells expressing CD30. The detectable label can be, e.g., a radioisotope, a fluorescent compound, an enzyme, or an enzyme co-factor.

B. Inhibition of Growth of CD30+ Cells

The antibodies can be used to inhibit or block CD30 function which, in turn, can be linked to the prevention or amelioration of certain disease symptoms, thereby implicating CD30 as being involved in the disease. Differences in CD30 expression during a disease state as compared to a non-disease state can be determined by contacting a test sample from a subject suffering from the disease and a control sample with the anti-CD30 antibody under conditions that allow for the formation of a complex between the antibody and CD30. Any complexes formed between the antibody and CD30 are detected and compared in the sample and the control.

For example, the antibodies can be used to elicit in vivo or in vitro one or more of the following biological activities: to inhibit the growth of and/or kill a cell expressing CD30; to mediate phagocytosis or ADCC of a cell expressing CD30 in the presence of human effector cells; to inhibit shedding of soluble CD30, to block CD30 ligand binding to CD30, to inhibit IL-4 expression or to mediate expression of the Th2 phenotype, e.g., at low dosages. As discussed herein, the defucosylated antibodies of the invention exhibit enhanced ADCC activity as compared to the fucosylated form of the antibody.

Accordingly, in another aspect, the invention provides a method of inhibiting growth of CD30$^+$ cells comprising contacting said cells with a defucosylated anti-CD30 antibody under conditions sufficient to induce antibody-dependent cellular cytoxicity (ADCC) of said cells. The cells can be, for example, tumor cells. In a preferred embodiment, the anti-CD30 antibody is a human antibody.

In one embodiment, the antibodies, or binding portions thereof, of the present invention can be used to modulate CD30 levels on target cells, such as by capping and eliminating receptors on the cell surface. Mixtures of anti-Fc receptor antibodies can also be used for this purpose.

Target-specific effector cells, e.g., effector cells linked to compositions of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD30, and to effect cell killing by, e.g., phagocytosis. Routes of administration can also vary.

Therapy with target-specific effector cells can be performed in conjunction with other techniques for removal of targeted cells. For example, anti-tumor therapy using the compositions of the invention and/or effector cells armed with these compositions can be used in conjunction with chemotherapy. Additionally, combination immunotherapy may be used to direct two distinct cytotoxic effector populations toward tumor cell rejection.

C. Use of Immunoconjugates and Combination Therapy

In one embodiment, immunoconjugates of the invention can be used to target compounds (e.g., therapeutic agents, labels, cytotoxins, radiotoxins immunosuppressants, etc.) to cells which have CD30 cell surface receptors by linking such compounds to the antibody. Thus, the invention also provides methods for localizing ex vivo or in vitro cells expressing CD30 (e.g., with a detectable label, such as a radioisotope, a fluorescent compound, an enzyme, or an enzyme co-factor). Alternatively, the immunoconjugates can be used to kill cells which have CD30 cell surface receptors by targeting cytotoxins or radiotoxins to CD30, such as to CD30-expressing tumor cells to thereby eliminate the tumor cell, or to CD30-expressing antigen-presenting cells to thereby eliminate the APCs as a means to inhibit immune responses (e.g., in autoimmune disorders).

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express CD30 can be induced to do so using lymphokine preparations. Lymphokine preparations can cause a more homogeneous expression of CD30 among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

In another embodiment, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the human antibodies. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the anti-CD30 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

D. Treatment of Autoimmune Diseases

The compositions can be used in vitro or in vivo to treat diseases mediated by or involving CD30, for example, diseases characterized by expression, typically overexpression, of CD30 such as autoimmune diseases mediated by macrophages, activated neutrophils, dendritic cells or NK cells, such as transplantation rejection, or Graft versus Host Disease (GVHD). Soluble CD30 is regularly shed from the surface of cells expressing CD30 and elevated sCD30 levels have been reported in the serum of patients with a variety of tumorigenic and autoimmune disorders. Accordingly, yet another use for the antibodies of the invention includes the prevention or treatment of diseases involving blocking or inhibiting of shedding of sCD30.

By contacting the antibody with CD30 (e.g., by administering the antibody to a subject), the ability of CD30 to induce such activities is inhibited and, thus, the associated disorder is treated. The antibody composition can be administered alone or along with another therapeutic agent, such as an immunosuppressant which acts in conjunction with or synergistically with the antibody composition to treat or prevent the CD30 mediated disease. Preferred antibodies bind to epitopes which are specific to CD30 and, thus, advantageously inhibit CD30 induced activities, but do not interfere with the activity of structurally related surface antigens. The compositions can be used to treat any diseases mediated by CD30 expressing cells, including, but not limited to, autoimmune hemolytic anemia (AIHA), rheumatoid arthritis (RA), systemic lupus erythematosus (SLE), Systemic Sclerosis, Atopic Dermatitis, Graves' disease, Hashimoto's thyroiditis, Wegner's granulomatosis, Omen's syndrome, chronic renal failure, idiopathic thrombocytopenic purpura (ITP), inflammatory bowel disease (IBD; including Crohn's Disease, Ulcerative Colitis and Celiac's Disease), insulin dependent diabetes mellitus (IDDM), acute infectious mononucleosis, HIV, herpes virus associated diseases, multiple sclerosis (MS), hemolytic anemia, thyroiditis, stiff man syndrome, pemphigus vulgaris and myasthenia gravis (MG).

E. Treatment of Cancer

In another embodiment, the present invention provides a method of inhibiting the growth of CD30+ tumor cells (i.e., tumor cells expressing CD30) in a subject, in which a defucosylated anti-CD30 antibody of the invention is administered to the subject such that growth of the CD30+ tumor cells is inhibited. For human subjects, the antibody preferably is a humanized or human antibody. In a preferred embodiment, the tumor cells are Hodgkin's Disease tumor cells. In another preferred embodiment, the tumor cells are anaplastic large-cell lymphomas (ALCL) tumor cells. In other embodiments, the tumor cells may be from a disease selected from the group consisting of non-Hodgkin's lymphoma, Burkitt's lymphoma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, adult T-cell lymphoma (ATL), HIV associated body cavity based lymphomas, Embryonal Carcinomas, undifferentiated carcinomas of the rhino-pharynx (e.g., Schmincke's tumor), Castleman's disease, Kaposi's Sarcoma and other CD30+ T-cell lymphomas and CD30+ B-cell lymphomas.

The method involves administering to a subject an antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the disease associated with CD30 expression.

Kits

Also within the scope of the invention are kits comprising an antibody of the invention and instructions for use. The kit can further contain one or more additional reagents, such as an immunostimulatory reagent, a cytotoxic agent or a radiotoxic agent, or one or more additional antibodies of the invention (e.g., an antibody having a complementary activity which binds to an epitope in the CD30 antigen distinct from the first antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all figures and all references, patents and published patent applications cited throughout this application are expressly incorporated herein by reference.

EXAMPLES

Example 1

Preparation and Characterization of Defucosylated Anti-CD30 Monoclonal Antibody

In this example, a fully human anti-CD30 monoclonal antibody was expressed in a cell line lacking a fucosyl transferase enzyme such that the cell line produces proteins lacking fucose in their carbohydrates. The defucosylated antibody was tested against a fucosylated anti-CD30 antibody (expressed in a different cell line that contains the fucosyl transferase enzyme) to determine structural and characteristic differences between the antibodies, using a variety of chemical analysis techniques, including capillary electrophoresis, comparison of amino acid sequence, mass differences by mass spectroscopy and charge variation by capillary isoelectric focusing.

The anti-CD30 fully human monoclonal antibody 5F11 was originally described in PCT Publication WO 03/059282. The amino acid and nucleotide sequences of the 5F11 heavy chain is shown in FIG. 1A and the amino acid and nucleotide sequences of the 5F11 light chain are shown in FIG. 1B. The 5F11 heavy and light chain variable sequences were subcloned into an expression vector. The 5F11 kappa variable region cDNA, including its signal sequence and an optimal Kozak sequence, was subcloned in frame with the human kappa constant region. The 5F11 heavy chain variable region cDNA, including its signal sequence and an optimal Kozak sequence, was subcloned in frame with the human γ1 heavy constant region. Both light and heavy chain expression were driven by human ubiquitin C promoters (Nenoi, M. et al. *Gene* 175:179, 1996). This expression vector is described in further detail in U.S. Patent Application Ser. No. 60/500,803, the contents of which are expressly incorporated herein by reference.

The expression vector was transfected into the FUT8$^{-/-}$ host cell line Ms704 by DNA electroporation. The Ms704 FUT8$^{-/-}$ cell line was created by the targeted disruption of the FUT8 gene in CHO/DG44 cells using two replacement vectors, and is more fully described in U.S. Patent Publication 20040110704 by Yamane et al. and Yamane-Ohnuki et al. (2004) *Biotechnol Bioeng* 87:614-22. The Ms704 cells were adapted to growth in suspension culture in growth medium, EX-CELL™ 325 PF CHO Medium (JRH #14335) supplemented with 100 µM hypoxanthine with 16 thymidine (Invitrogen #11067-030) and 6 mM L-glutamine (Invitrogen #25030-081).

The vector DNA to be used for electroporation was ethanol precipitated and resuspended in 10 mM Tris 7.6, 1 mM EDTA. 1, 5, 10, 15 or 20 µg DNA was utilized for twenty electroporations, four electroporations per DNA concentration. The Ms704 cells were prepared for transfection by washing the cells in a sucrose-buffered solution (SBS) and resuspending the cells at 1×10$^7$ cells/ml SBS solution. 400 µl cells were mixed with construct DNA and electroporated utilizing settings at 230 volts, 400 microfaradays capacitance and 13 ohms resistance (BTX Molecular Delivery Systems #600 electro cell manipulator). The cells were removed from the electroporation cuvettes and 20 ml growth medium was added. The cells were plated into a 96 well dish using 200 µl cells per well, approximately 4×10$^4$ cells/well. 2 days after the electroporation, 150 µl of medium was removed from each well and replaced with 150 µl selection medium, growth medium with 400 µg/ml G418 (Invitrogen #10131-035). Every three to seven days, 150 µl of selection medium per well was replaced with fresh selection medium. CHO DG44 host cells (FUT 8+/+) were electroporated with the identical 5F11 construct using a similar procedure and CHO DG44 transfectants expressing recombinant 5F11 antibody containing fucosylated carbohydrates were established.

The highest producing Ms704 and CHO DG44 clones were expanded and recombinant 5F11 antibody was purified from cell culture supernatants by Protein A affinity chromatography.

Comparative analysis of N-linked oligosaccharides derived from the Ms704 and the CHO DG44 derived anti-CD30 monoclonal antibody samples was done by capillary electrophoresis laser induced fluorescence (cLIF) (Chen and Evangelista (1998) *Electrophoresis* 15:1892). The N-linked oligosaccharides of the purified antibody were released by adding the peptide N-glycanase (Prozyme) and incubating overnight. The protein was ethanol precipitated, and the carbohydrate containing supernatant was transferred to a new tube and dried using a Speedvac. The carbohydrates were resuspended and derivatized with 8-aminopyrene-1,3,6-trisulfonate (APTS) under mild reductive amination conditions in which desialylation and loss of fucose residues was minimized. The reaction adducts were analyzed by capillary electrophoresis with a laser-induced fluorescence detector (Beckman Coulter) (Ma and Nashabeh (1999) *Anal. Chem.* 71:5185). Differences in the oligosaccharide profile were observed between the antibody obtained from the Ms704 cell line as compared to the CHO DG44 cell line, consistent with an absence of fucose residues in the Ms704 derived anti-CD30 antibodies.

To confirm the absence of fucose residues on the antibody expressed in Ms704 cells, monosaccharide composition analysis was performed. The results are shown below in Table 1:

TABLE 1

Monosaccharide Analysis

| Antibody | Protein Amount (µg) | Monosaccharide | Amount Found (pmol) | mol Sugar/ mol Protein |
| --- | --- | --- | --- | --- |
| Anti-CD30 + fucose | 29 µg | Fucose | 206.0 | 1.0 |
| | | Galactosamine | 0.0 | 0.0 |
| | | Glucosamine | 847.6 | 4.4 |
| | | Galactose | 85.8 | 0.5 |
| | | Mannose | 547.0 | 2.9 |
| Anti-CD30 − fucose | 23 µg | Fucose | 0.0 | 0.0 |
| | | Galactosamine | 0.0 | 0.0 |
| | | Glucosamine | 655.2 | 4.3 |
| | | Galactose | 89.7 | 0.6 |
| | | Mannose | 488.8 | 3.2 |

The results of the monosaccharide analysis confirm that the antibody expressed in Ms704 cells lacks fucosyl residues.

Aside from the difference in oligosaccharides shown by capillary electrophoresis and monosaccharide analysis, the Ms704 and CHO DG44 derived anti-CD30 antibody protein samples were essentially identical. Analysis of N-terminal protein sequence revealed an identical N-terminal amino acid sequence. Mass spectroscopy of the light chain of the Ms704 and CHO DG44 derived anti-CD30 antibodies yielded masses of 23,740 and 23,742, respectively, which were within the error of the instrument. The two antibodies were also tested using a standard capillary isoelectric focusing kit assay (Beckman Coulter) and showed that the two antibody samples had an identical isoelectric point at 8.6. These studies indicate that the protein component of the antibody samples derived from the Ms704 and the CHO DG44 cells are essentially identical with the exception of the defucosylation of the carbohydrate component of the Ms704 derived antibodies.

Example 2

Assessment of ADCC Activity of Defucosylated Anti-CD30 Antibody

The anti-CD30 monoclonal antibody 5F11 is capable of killing CD30+ cells through the recruitment of an effector cell population via antibody dependent cellular cytotoxicity (ADCC). In this example, defucosylated 5F11 (defuc-5F11) monoclonal antibodies were tested for the ability to kill CD30+ cell lines in the presence of effector cells in a cytotoxicity chromium release assay.

Human effector cells were prepared from whole blood as follows. Human peripheral blood mononuclear cells were purified from heparinized whole blood by standard Ficoll-paque separation. The cells were resuspended in RPMI1640 media containing 10% FBS and 200 U/ml of human IL-2 and incubated overnight at 37° C. The following day, the cells were collected and washed once in culture media and resuspended at 1×10$^7$ cells/ml. Two million target CD30+ cells were incubated with 200 µCi $^{51}$Cr in 1 ml total volume for 1 hour at 37° C. The target cells were washed once, resuspended in 1 ml of media, and incubated at 37° C. for an additional 30 minutes. After the final incubation, the target cells were washed once and brought to a final volume of 1×10$^5$ cells/ml.

The CD30+ cell lines L540 (human Hodgkin's lymphoma; DSMZ Deposit No. ACC 72), L428 (human Hodgkin's lymphoma; DSMZ Deposit No. ACC 197), L1236 (human Hodgkin's lymphoma; DSMZ Deposit No. ACC 530) and Karpas (human T cell lymphoma; DSMZ Deposit No. ACC 31) cell lines were initially tested for binding to both the fucosylated 5F11 (fuc-5F11) and defuc-5F11 using a standard FACS analysis. Each target cell displayed similar binding profiles through a range of antibody concentrations for both fuc-5F11 and defuc-5F11. The level of CD30 expression, as determined by mean fluorescence intensity, was highest in L540, followed by Karpas, L428, and the lowest CD30 expression was on L1236 cells.

The L540, L428, L1236 and Karpas cells were tested in a modified $^{51}$Cr antibody dependent cellular cytotoxicity (ADCC) assay as follows. Each target cell line (100 µl of labeled CD30+ cells) was incubated with 50 µl of effector cells and 50 µl of antibody. A target to effector ratio of 1:50 was used throughout the experiments. In all studies, the following negative controls were also run: a) target and effector cells without antibody, b) target cells without effector cells, c) wells containing target and effector cells in the presence of 1% Triton X-100, and d) human IgG1 isotype control. Following a 4 hour incubation at 37° C., the supernatants were collected and counted on a gamma Counter (Cobra II auto-gamma from Packard Instruments) with a reading window of 240-400 keV. The counts per minute were plotted as a function of antibody concentration and the data was analyzed by non-linear regression, sigmoidal dose response (variable slope) using Prism software (San Diego, Calif.). Cell cytotoxicity curves for the L540, L428, L1236 and Karpas cell lines using varying concentrations of fuc-5F11 and defuc-5F11 are shown in FIGS. 4-7, respectively.

The percent lysis was determined by the following equation:

% Lysis=(Sample CPM−no antibody CPM)/TritonX CPM−No antibody CPM)×100

The % Lysis was tested at an antibody concentration of 25 μg/ml and a target to effector cell ratio of 1:50. $EC_{50}$ values also were calculated for each target cell. The results are summarized in Table 2 below.

TABLE 2

Cytotoxic Ability of Defucosylated Anti-CD30 Monoclonal Antibody

| Target cell | % Lysis Fucose+ | % Lysis Fucose− | % Lysis ratio fucose−:fucose+ | $EC_{50}$ (μg/ml) Fucose+ | $EC_{50}$ (μg/ml) Fucose− | $EC_{50}$ ratio fucose+:fucose− |
|---|---|---|---|---|---|---|
| L540 | 42 | 68 | 1.61 | 0.042 | 0.009 | 4.7 |
| Karpas | 19 | 50 | 2.63 | 0.250 | 0.032 | 7.8 |
| L428 | 20 | 43 | 2.15 | 0.100 | 0.009 | 11.1 |
| L1236 | 4 | 13 | 3.25 | 1.218 | 0.045 | 27.1 |

Defuc-5F11 showed from 1.61 times (for L540 cells) to 3.25 times (for L1236 cells) greater percent cell lysis as compared to the fuc-5F11 antibody. This increased potency of the defuc-5F11 results in measurable cell lysis at antibody concentrations where the fuc-5F11 has no measurable effect. For example, on L1236 cells, which have a low level of expression of CD30, defuc-5F11 at 0.1 μg/ml results in a 10% specific lysis, whereas fuc-5F11 at the same concentration has no measurable effect (see FIG. 6). Defuc-5F11 was 4.7 times (for L540 cells) to 27.1 times (for L1236 cells) more potent in ADCC activity than the fuc-5F11 antibody, as measured by ratio of $EC_{50}$ values.

Example 3

Assessment of ADCC Activity of Anti-CD30 Antibody

Figure 9:
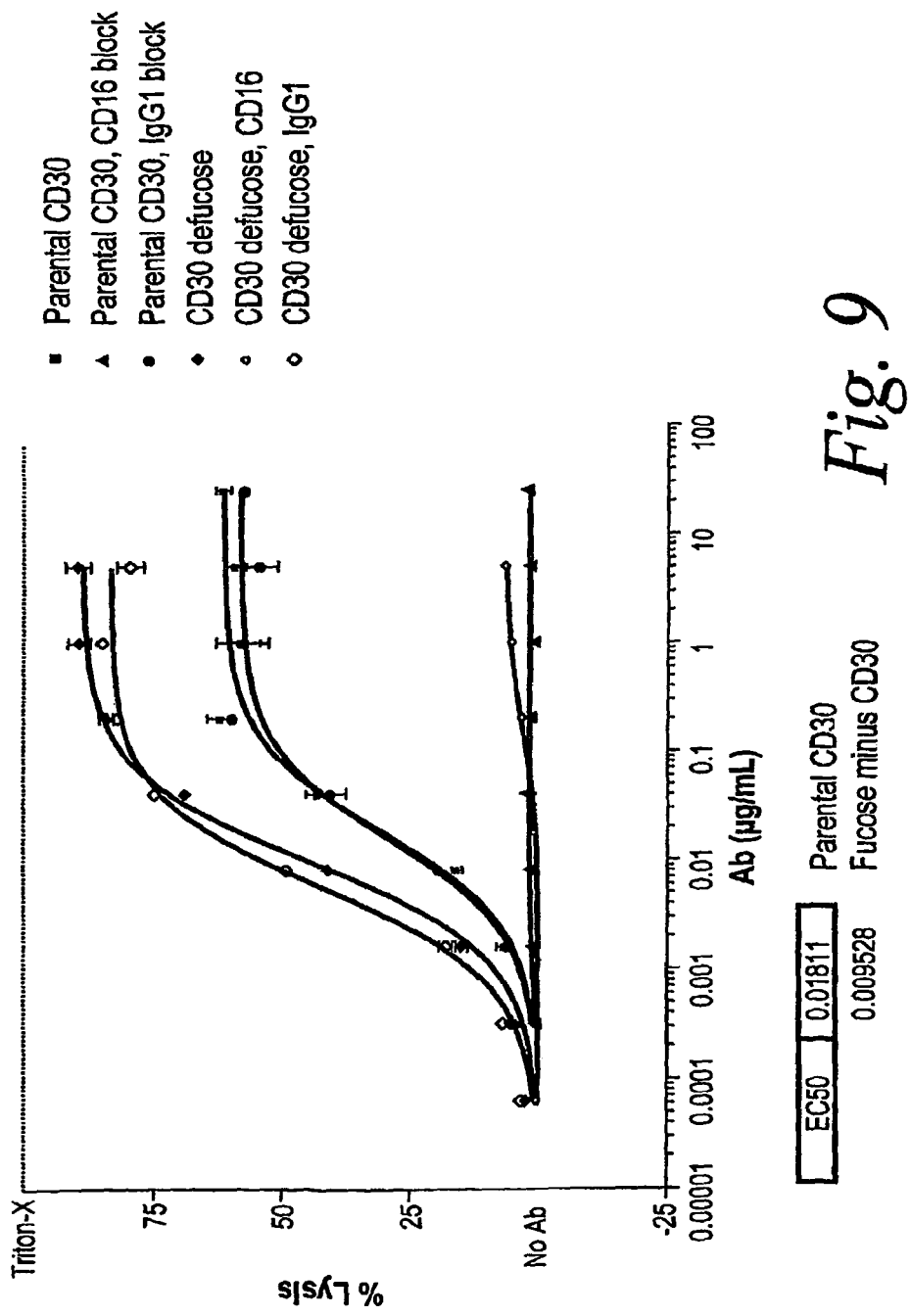
FIG. 9 is a graph showing blockade of ADCC activity with an anti-CD16 antibody.

In this example, anti-CD30 monoclonal antibodies were tested for the ability to kill CD30+ cell lines in the presence of effector cells via antibody dependent cellular cytotoxicity (ADCC) in a fluorescence cytotoxicity assay. Human effector cells were prepared as described above and the ADCC assay performed as indicated above. As can be seen in FIG. 9, when using the defucosylated anti-CD30 antibody there was increased ADCC activity as compared with parental anti-CD30 antibody. In addition, the defucosylated anti-CD30 antibody was more potent than the parental antibody as evidenced by the reduced EC50 as compared to the parental anti-CD30 antibody. The antibody was also more efficacious as evidenced by the fact that the maximum percent lysis was higher for the defucosylated anti-CD30 antibody. With either antibody, the anti-CD16 (3G8) antibody effectively inhibited the ADCC suggesting that this lysis was mediated by CD16.

Example 4

Increased ADCC with Human Effector Cells

ADCC assays were performed as described above. In this experiment, however, mouse effector cells were compared with human effector cells. As can be seen in FIG. 10, while there was no increased ADCC comparing parental anti-CD30 antibody with defucosylated antibody when mouse effector cells were used, when human effector cells were examined, there was a notable increase in ADCC with the defucosylated antibody as compared to the parental anti-CD30 antibody.

Example 5

ADCC Assay Comparing Parental and Defucosylated Antibody Using Effector Cells from Cynomolgus Monkeys Whole blood was obtained from cynomolgus monkeys. Red blood cell lysed cynomolgus peripheral blood cells were stimulated with 50 U/ml rIL-2 and cultured in RPMI1640 media containing 10% FBS overnight at 37° C. On the day of the study, cynomolgus cells were resuspended in assay buffer (RPMI1640, 10% FBS, 2.5 mM probenecid) at $1\times10^7$ cells/mL. CD30 positive target cells, Karpas 299, were labeled, washed three times with wash buffer (PBS, 2.5 mM probenecid, 20 mM HEPES), and adjusted to $1\times10^5$ cells/mL for 1:50 target to effector cell ratio. The ADCC assay was performed as described above. We compared the activity of parental anti-CD30 antibody to defucosylated antibody using effector cells purified from cynomolgus blood. Modest ADCC activity was seen with the parental antibody (from around 7-10% cell lysis at 10 μg/mL). In contrast, the defucosylated antibody induced significantly higher percent lysis (from around 10-30% cell lysis at 10 μg/mL) and a reduced EC50 (see FIG. 11).

Example 6

Scatchard Analysis of Binding Affinity of Anti-CD30 Monoclonal Antibodies to L540 Cells, Activated Human and Cynomolgus Peripheral Blood Cells The binding affinity of the parental and defucosylated anti-CD30 antibodies was determined. We compared the binding affinity of the two antibodies to CD30 positive L540 cells as well as PHA/Con A-activated human or cynomolgus peripheral blood mononuclear cells.

Human or cynomolgus peripheral blood cells were stimulated with 2 μg/ml PHA, 10 μg/ml Con A, and 50 U/ml rIL-2 and cultured in RPMI1640 media containing 10% fetal bovine serum (FBS) at $1\times10^6$ cells/ml density for 3 days. On the day of the study, the cells were washed and adjusted to $2\times10^7$ cells/ml in binding buffer (RPMI1640+10% FBS). As a control, CD30 positive L540 cells (adjusted to $4\text{-}8\times10^6$ cells/ml) were used in these studies since they express high levels of the antigen. The cells were placed on ice until the initiation of the experiment. Millipore glass fiber filter plates (MAFBNOB50) were coated with 1% nonfat dry milk in water and stored a 4° C. overnight. The plates were washed three times with 0.2 ml of binding buffer. Fifty microliters of buffer alone was added to the maximum binding wells (total binding). Twenty-five microliters of buffer alone was added to the control wells. Varying concentration of $^{125}$I-anti-CD30 antibody was added to all wells in a volume of 25 µl. Varying concentrations of unlabeled antibody at 300-400 fold excess were added in a volume of 25 µl to control wells (non-specific binding) and 25 µl of CD30 positive L540 cells or stimulated human or cynomolgus peripheral blood cells in binding buffer were added to all wells. The plates were incubated for 2 hours at 200 RPM on a shaker at 4° C. At the completion of the incubation the Millipore plates were washed twice with 0.2 ml of cold wash buffer (RPMI1640, 10% FBS, 500 mM NaCl). The filters were removed and counted in a gamma counter. Evaluation of equilibrium binding was performed using single site binding parameters with the Prism software (San Diego, Calif.).

Using the above Scatchard binding assay, the $K_D$ of the parental CD30 antibody for L540 cells was approximately 1.4 nM while the defucosylated antibody had a $K_D$ of 1.9 nM (Table 3). This indicates that there was little change in affinity with removal of fucose. These studies were repeated using primary cells rather than a cell line. In addition, the affinity on cells which express significantly fewer receptors per cell was tested. Activated human peripheral blood cells were prepared as indicated above and the $K_D$ was found to be 1.1 and 2.7 nM for parental and defucosylated anti-CD30 antibody, respectively.

Finally, the binding affinity of the parental and defucosylated antibody for PHA, Con A, and rIL-2 activated cynomolgus peripheral blood mononuclear cells was compared. The $K_D$ was found to be approximately 0.47 nM and 0.83 nM for parental and defucosylated antibody, respectively.

TABLE 3

| Scatchard Analysis | | | | |
|---|---|---|---|---|
| Sample | | L540 | Human | Cynomolgus |
| Parental CD30 | KD (nM ave) | 1.37 | 1.08 | 0.47 |
| | Receptors Per Cell (ave) | 2496082 | 45654 | 72781 |
| Defucosylated CD30 | KD (nM ave) | 1.93 | 2.66 | 0.83 |
| | Receptors Per Cell (ave) | 3024600 | 74258 | 108824 |

EQUIVALENTS

Those skilled in the art will recognize, or be able to ascertain using no more than routine experimentation, many equivalents of the specific embodiments of the invention described herein. Such equivalents are intended to be encompassed by the following claims.

| SUMMARY OF SEQUENCE LISTING | |
|---|---|
| SEQ ID NO: | SEQUENCE |
| 1 | VH a.a. 5F11 |
| 2 | VH a.a. 17G1 |
| 3 | VH a.a. 2H9 |
| 4 | VK a.a. 5F11 |
| 5 | VK a.a. 17G1 |
| 6 | VK a.a. 2H9 |
| 7 | VH CDR1 a.a. 5F11 |
| 8 | VH CDR1 a.a. 17G1 |
| 9 | VH CDR1 a.a. 2H9 |
| 10 | VH CDR2 a.a. 5F11 |
| 11 | VH CDR2 a.a. 17G1 |
| 12 | VH CDR2 a.a. 2H9 |
| 13 | VH CDR3 a.a. 5F11 |
| 14 | VH CDR3 a.a. 17G1 |
| 15 | VH CDR3 a.a. 2H9 |
| 16 | VK CDR1 a.a. 5F11 |
| 17 | VK CDR1 a.a. 17G1 |
| 18 | VK CDR1 a.a. 2H9 |
| 19 | VK CDR2 a.a. 5F11 |
| 20 | VK CDR2 a.a. 17G1 |
| 21 | VK CDR2 a.a. 2H9 |
| 22 | VK CDR3 a.a. 5F11 |
| 23 | VK CDR3 a.a. 17G1 |
| 24 | VK CDR3 a.a. 2H9 |
| 25 | VH 4-34 germline aa |
| 26 | VH 3-07 germline aa |
| 27 | VK L15 germline aa |
| 28 | VK A27 germline aa |
| 29 | VK L6 germline aa |
| 30 | VH n.t. 5F11 |
| 31 | VH n.t. 17G1 |
| 32 | VH n.t. 2H9 |
| 33 | VK n.t. 5F11 |
| 34 | VK n.t. 17G1 |
| 35 | VK n.t. 2H9 |

The invention claimed is:

1. A method of inhibiting growth or activity of CD30+ cells comprising contacting the cells with an isolated full length IgG1 anti-CD30 antibody, which lacks fucose residues, under conditions sufficient to induce antibody-dependent cellular cytotoxicity (ADCC) of the cells, wherein the antibody comprises: (a) a heavy chain variable region CDR1 comprising SEQ ID NO:7, a heavy chain variable region CDR2 comprising SEQ ID NO:10, a heavy chain variable region CDR3 comprising SEQ ID NO:13, a light chain variable region CDR1 comprising SEQ ID NO:16, a light chain variable region CDR2 comprising SEQ ID NO:19; and a light chain variable region CDR3 comprising SEQ ID NO:22.

2. A method of inhibiting growth or activity of CD30+ cells comprising contacting the cells with an isolated full length IgG1 anti-CD30 antibody, which lacks fucose residues, under conditions sufficient to induce antibody-dependent cellular cytotoxicity (ADCC) of the cells, wherein the antibody comprises a heavy chain variable region comprising SEQ ID NO: 1 and a light chain variable region comprising SEQ ID NO: 4.

3. The method of claim 1, wherein the antibody is a monoclonal antibody.

4. The method of claim 1, wherein the antibody is a human, humanized, or chimeric antibody.

5. The method of claim 1, wherein the antibody is linked to a cytotoxic agent.

6. The method of claim 1, wherein the CD30+ cells mediate an autoimmune disease.

7. The method of claim 6, wherein the autoimmune disease is selected from the group consisting of autoimmune hemolytic anemia (AIHA), rheumatoid arthritis (RA), systemic lupus erythematosus (SLE), Systemic Sclerosis, Atopic Dermatitis, Graves' disease, Hashimoto's thyroiditis, Wegner's granulomatosis, Omen's syndrome, chronic renal failure, idiopathic thrombocytopenic purpura (ITP), Crohn's Disease, Ulcerative Colitis, Celiac's Disease, insulin dependent diabetes mellitus (IDDM), acute infectious mononucleosis, HIV, herpes virus associated diseases, multiple sclerosis (MS), hemolytic anemia, thyroiditis, stiff man syndrome, pemphigus vulgaris and myasthenia gravis (MG).

8. The method of claim 7 wherein the autoimmune disease is ulcerative colitis.

9. The method of claim 7, wherein the autoimmune disease is Crohn's Disease.

10. The method of claim 2, wherein the antibody is a monoclonal antibody.

11. The method of claim 2, wherein the antibody is a human, humanized, or chimeric antibody.

12. The method of claim 2, wherein the antibody is linked to a cytotoxic agent.

13. The method of claim 2, wherein the CD30+ cells mediate an autoimmune disease.

14. The method of claim 13, wherein the autoimmune disease is selected from the group consisting of autoimmune hemolytic anemia (AIHA), rheumatoid arthritis (RA), systemic lupus erythematosus (SLE), Systemic Sclerosis, Atopic Dermatitis, Graves' disease, Hashimoto's thyroiditis, Wegner's granulomatosis, Omen's syndrome, chronic renal failure, idiopathic thrombocytopenic purpura (ITP), Crohn's Disease, Ulcerative Colitis, Celiac's Disease, insulin dependent diabetes mellitus (IDDM), acute infectious mononucleosis, HIV, herpes virus associated diseases, multiple sclerosis (MS), hemolytic anemia, thyroiditis, stiff man syndrome, pemphigus vulgaris and myasthenia gravis (MG).

15. The method of claim 14 wherein the autoimmune disease is ulcerative colitis.

16. The method of claim 14, wherein the autoimmune disease is Crohn's Disease.

* * * * *